(12) United States Patent
Belson et al.

(10) Patent No.: US 11,857,786 B2
(45) Date of Patent: *Jan. 2, 2024

(54) METHOD AND DEVICE FOR TRANSDERMALLY APPLYING ELECTRICAL STIMULATION TO A REGION OF THE HEAD HAVING HIGH IMPEDANCE

(71) Applicant: NEUROLIEF LTD., Yokneam Illit (IL)

(72) Inventors: Ron Belson, Tel Aviv (IL); Yaniv Matza, Kfar Saba (IL); Amit Dar, Kfar-Hess (IL); Amir Cohen, Ra'anana (IL)

(73) Assignee: NEUROLIEF LTD., Yokneam Illit (IL)

( * ) Notice: Subject to any disclaimer, the term of this patent is extended or adjusted under 35 U.S.C. 154(b) by 162 days.

This patent is subject to a terminal disclaimer.

(21) Appl. No.: 17/469,640

(22) Filed: Sep. 8, 2021

(65) Prior Publication Data
US 2022/0001180 A1   Jan. 6, 2022

Related U.S. Application Data

(63) Continuation of application No. 16/093,094, filed as application No. PCT/IB2017/052045 on Apr. 9, 2017, now Pat. No. 11,154,710.
(Continued)

(51) Int. Cl.
*A61N 1/36* (2006.01)
*A61B 5/0531* (2021.01)
(Continued)

(52) U.S. Cl.
CPC ........ *A61N 1/36034* (2017.08); *A61B 5/0531* (2013.01); *A61B 5/4836* (2013.01);
(Continued)

(58) Field of Classification Search
CPC .... A61N 1/36034; A61N 1/00; A61N 1/0456; A61N 1/0476; A61N 1/0484; A61N 1/06;
(Continued)

(56) References Cited

U.S. PATENT DOCUMENTS

| 4,638,807 A | 1/1987 | Ryder |
| 6,871,090 B1 | 3/2005 | He et al. |

(Continued)

FOREIGN PATENT DOCUMENTS

| AU | 2015227382 A1 | 10/2015 |
| EP | 1070518 A2 | 1/2001 |

(Continued)

OTHER PUBLICATIONS

International Search Report for PCT/IB2017/052045 dated Jul. 17, 2017.
Written Opinion for PCT/IB2017/052045 dated Jul. 17, 2017.

*Primary Examiner* — Gary Jackson
*Assistant Examiner* — Alexander M Eisenberg
(74) *Attorney, Agent, or Firm* — Momentum IP; Marc Van Dyke

(57) ABSTRACT

A method and apparatus for transdermally providing electrical current to a region of a user's head at high impedance conditions, while maintaining low voltage levels.

20 Claims, 7 Drawing Sheets

Related U.S. Application Data

(60) Provisional application No. 62/322,498, filed on Apr. 14, 2016.

(51) Int. Cl.
*A61B 5/00* (2006.01)
*A61N 1/04* (2006.01)
*A61N 1/06* (2006.01)
*A61N 1/00* (2006.01)

(52) U.S. Cl.
CPC ............ *A61N 1/00* (2013.01); *A61N 1/0456* (2013.01); *A61N 1/0476* (2013.01); *A61N 1/0484* (2013.01); *A61N 1/06* (2013.01); *A61N 1/36021* (2013.01); *A61N 1/36025* (2013.01); *A61N 1/36075* (2013.01)

(58) Field of Classification Search
CPC ............ A61N 1/36021; A61N 1/36025; A61N 1/36075; A61B 5/0531; A61B 5/4836
See application file for complete search history.

(56) References Cited

U.S. PATENT DOCUMENTS

| | | |
|---|---|---|
| 9,020,590 B1 | 4/2015 | Honeycutt et al. |
| 11,154,710 B2 | 10/2021 | Belson et al. |
| 2005/0113880 A1 | 5/2005 | Gordon |
| 2006/0173493 A1* | 8/2006 | Armstrong ......... A61N 1/36157 607/45 |
| 2006/0293720 A1 | 12/2006 | DiLorenzo |
| 2008/0221642 A1 | 9/2008 | Humayun |
| 2010/0152817 A1 | 6/2010 | Gillbe |
| 2011/0054564 A1 | 3/2011 | Valencia |
| 2011/0082524 A1 | 4/2011 | Thomas et al. |
| 2013/0238048 A1* | 9/2013 | Almendinger ....... A61N 1/0509 607/40 |
| 2013/0303828 A1 | 11/2013 | Hargrove |
| 2014/0039579 A1 | 2/2014 | Mashiach |
| 2014/0081353 A1 | 3/2014 | Cook |
| 2014/0163644 A1 | 6/2014 | Scott |
| 2014/0180364 A1 | 6/2014 | Armstrong |
| 2014/0214119 A1 | 7/2014 | Greiner et al. |
| 2014/0277274 A1 | 9/2014 | Seligman |
| 2015/0238762 A1 | 8/2015 | Pal |
| 2015/0374971 A1 | 12/2015 | Dar et al. |
| 2019/0022372 A1 | 1/2019 | Dar et al. |

FOREIGN PATENT DOCUMENTS

| | | |
|---|---|---|
| EP | 2173435 B1 | 10/2015 |
| EP | 2981326 A1 | 2/2016 |
| WO | 2014141213 A1 | 9/2014 |
| WO | 2016042499 A1 | 3/2016 |

* cited by examiner

METHOD AND DEVICE FOR TRANSDERMALLY APPLYING ELECTRICAL STIMULATION TO A REGION OF THE HEAD HAVING HIGH IMPEDANCE

RELATED APPLICATION

PCT/IB2017/052045 filed on Apr. 9, 2017 is incorporated by reference in its entirety.

FIELD OF THE INVENTION

The present invention relates to apparatus and methods for applying electrical stimulation to the head region, and particularly to areas having high impedance, such as hair covered head regions.

BACKGROUND OF THE INVENTION

The present invention relates to apparatus and methods for applying electrical stimulation to the head region. The disclosed apparatus may be used for stimulation of peripheral and cranial nerves, for transcranial stimulation of brain regions, and for sensing various body parameters.

Peripheral and cranial nerves in the head region may be stimulated to treat various conditions such as chronic pain, migraine, tension headaches, cluster headaches, fibromyalgia, depression, post-traumatic stress disorder (PTSD), anxiety, stress, bipolar disorder, schizophrenia, obsessive compulsive disorder (OCD), insomnia, epilepsy, attention deficit disorder (ADD), attention deficit hyperactivity disorder (ADHD), Parkinson's disease, Alzheimer's disease, obesity, multiple sclerosis, stroke and traumatic brain injury (TBI). The anatomy of peripheral and cranial nerves in the head region, such as that of the occipital and trigeminal nerves, and their projections to brainstem regions such as the locus coeruleus and nucleus raphe magnus, as well as to higher brain regions such as the thalamus and anterior cingulate cortex, may be advantageous when stimulating these nerves for treatment of such conditions.

Neurostimulation of superficial nerves in the head region, such as the occipital, supraorbital, supratrochlear, zygomaticotemporal, and auriculotemporal nerve branches, can be applied either invasively or non-invasively. Due to the challenge of transferring current through the hair, stimulation of cephalic nerves which lie under hair covered regions such as the occipital nerve (greater, lesser and third occipital branches), is typically carried out using implanted or percutaneous nerve stimulators. Such devices include electrodes that are inserted under the scalp and thus bypass the high impedance barrier formed by the hair and scalp. However, implanted nerve stimulation remains an invasive and costly procedure with a high rate of complications including infection, bleeding or fluid collection under the skin, as well as hardware-related malfunctions such as migration and breakage of the implanted leads and pulse generator failure. Transdermal stimulation of cephalic nerves such as the occipital nerve branches using non-invasive techniques is likely to achieve similar clinical benefits to those of implanted stimulators without the risks and cost associated with an invasive procedure.

Non-invasive application of electrical current to the head, and specifically to regions that are covered by hair, poses numerous challenges. The hair and scalp create a high impedance barrier which makes it difficult to transfer electrical current to underlying nerves. High sensory sensitivity of the scalp and of the periosteum of the skull bone, as well as dermal vulnerability of the scalp tissue to electrical current, are additional considerations while attempting to non-invasively stimulate cephalic nerves.

The relationship between the current provided to a tissue, the impedance in the tissue, and the voltage required to provide the current, is characterized by Ohm's Law: $V = I \cdot Z$, where V (voltage) is the potential difference between two electrodes placed over the head, Z is the impedance of the hair and scalp tissue, and I is the current flowing through the impedance. Thus, the voltage increases substantially proportionally to the impedance or resistance.

Non-invasive stimulation of nerves, such as the greater occipital, requires substantial current amplitude (3-15 mA), and high voltage levels (up to 150V) may be needed to transfer the current through the hair and scalp due to the high impedance associated therewith. Such high voltage levels are disadvantageous as they may injure the scalp tissue, be uncomfortable for the user, and/or may be wasteful in consumption of energy so that a large battery may be required in order to enable sufficient treatment time.

The impedance level varies significantly between people and tends to change with time. Several factors were identified as affecting the impedance level: Non-dynamic factors, or factors related to differences between people, include:
  Capacitive/resistive characteristics of the scalp, for example, the resistive component may be $5K\Omega$ in some people and may reach $20K\Omega$ in others.
  Type of hair, for example, oily hair tends to absorb less water than dry hair and thereby have higher impedance than dry hair.
  Amount and density of hair, for example, denser hair creates higher impedance barrier between the stimulating electrode and the scalp.

Dynamic factors, which may vary between treatments and/or during a specific treatment for the same person, include:
  Proximity and quality of contact between the stimulating electrode and the scalp, which may be affected by the skill of the user when attaching the electrodes, or by changes in the user's position. For example, when the user is supine and the weight of his head presses the occipital electrodes against the surface, the stimulating electrode will be closer to the scalp, so that the impedance will be lower.
  Absorption of conductive medium of the electrodes by the hair. For example, conductive media such as water, saline or conductive gel applied to the electrodes to enhance the flow of current therethrough may gradually be absorbed by the user's hair, thus reducing the resistance of the hair to the flow of current and thereby increasing the conductivity between the electrodes and the scalp.
  Dehydration of the conductive medium, which may be affected by the duration of treatment, environmental conditions, and the like.
  Pressure applied on the electrodes pushing them toward the scalp, for example by adjustment of the headset, by the position of the user, and the like.

Variations to the impedance, and specifically dynamic variations of the impedance in the electrode-scalp interface, may disadvantageously affect the ability to achieve effective and homogeneous stimulation of the target nerves or brain regions and may require constant attention and high skillfulness of the user when operating the device.

There is therefore a recognized need for, and it would be highly advantageous to have, a system and method for effective non-invasive neurostimulation of the head region, specifically at areas that are covered by hair, which system and method monitor the tissue and adapt the output signal to the user's characteristics and to changes over time. It would be of particular advantage for such a system and method to avoid damage to scalp tissue as well as discomfort to the user, and to operate in a safe and robust fashion.

SUMMARY OF THE INVENTION

According to some teachings of the present invention there is provided a method for transdermally applying electrical stimulation to a region of the head of a user, the method including:
(a) engaging at least two electrodes with a surface of the scalp of the user, the electrodes being functionally associated with an electronic circuit having a compliance voltage;
(b) delivering via the engaged electrodes a balanced pulse including a positive phase train including a streak of constant current positive phases separated by rest times, the positive phase train immediately followed by a negative phase train including a streak of constant current negative phases separated by rest times, each of the positive phases and the negative phases is intended to provide a predetermined amount of charge to the head of the user, wherein:
 each of a first time ratio, between a cumulative duration of the rest times between the positive phases in the positive phase train and a cumulative duration of the positive phases, and a second time ratio, between a cumulative duration of the rest times between the negative phases in the negative phase train and a cumulative duration of the negative phases is smaller than a predetermined threshold ratio;
 the positive phases and the negative phases have a common phase width $w_l$; and
 the rest times between immediate successor phases in the positive phase train and in the negative phase train having a common rest-time value $rt^l$;
(c) monitoring an amount of charge delivered by the positive phases and the negative phases, to identify a reduction of charge delivered by one or more of the positive and the negative phases:
(d) upon identification of a reduction, adapting the common rest time value $rt^l$; and
(e) repeating steps (b)-(d) until:
 the monitoring shows that the predetermined amount of charge has been provided by each of the positive and the negative phases; or
 at least one of the first time ratio and the second time ratio reaches the predetermined threshold ratio and a voltage of the balanced pulse reaches a predetermined voltage threshold.

In some embodiments, when each of the first and the second time ratios is less than the predetermined threshold ratio, the adapting includes increasing the common rest-time value, and when each of the first and the second time ratios is equal to or greater than the predetermined threshold ratio, the adapting includes increasing a voltage provided by the electrodes and decreasing the common rest time value to a predetermined minimum rest-time value.

In some embodiments, the adapting further includes adapting the common phase width.

According to some teachings of the present invention there is provided a method for transdermally applying electrical stimulation to a region of the head of a user, the method including:
(a) engaging at least two electrodes with a surface of the scalp of the user, the electrodes being functionally associated with an electronic circuit having a compliance voltage;
(b) delivering via the engaged electrodes a balanced pulse including a positive phase train including a streak of constant current positive phases separated by rest times, the positive phase train immediately followed by a negative phase train including a streak of constant current negative phases separated by rest times, each of the positive phases and the negative phases intended to provide a predetermined amount of charge to the head of the user, wherein each of a first time ratio, between a cumulative duration of the rest times between the positive phases in the positive phase train and a cumulative duration of the positive phases, and a second time ratio, between a cumulative duration of the rest times between the negative phases in the negative phase train and a cumulative duration of the negative phases is smaller than a predetermined threshold ratio;
(c) monitoring an amount of charge delivered by the positive phases and the negative phases, to identify a reduction of charge delivered by one or more of the positive and the negative phases:
(d) upon identification of a reduction, adapting at least one the rest time in at least one of the positive phase train and the negative phase train; and
(e) repeating steps (b)-(d) until:
 the monitoring shows that the predetermined amount of charge has been provided by each of the positive and the negative phases; or
 at least one of the first time ratio and the second time ratio reaches the predetermined threshold ratio and a voltage of the balanced pulse reaches a predetermined voltage threshold.

In some embodiments, the positive phases in the positive phase train have a common phase width $w_p$. In some embodiments, the negative phases in the negative phase train have a common phase width $w_n$. In some embodiments, the positive phases in the positive phase train and the negative phases in the negative phase train have a common phase width $w_l$.

In some embodiments, rest times between immediate successor phases in the positive phase train have a common rest-time value $rt^p$. In some embodiments, the rest times between immediate successor phases in the negative phase train have a common rest-time value $rt^n$. In some embodiments, the rest times between immediate successor phases in the positive phase train and in the negative phase train have a common rest-time value $rt^l$.

In some embodiments, when each of the first and the second time ratio is less than the predetermined threshold ratio, the adapting includes increasing a duration of the at least one the rest-time, and when each of the first and the second time ratio is equal to or greater than the predetermined threshold ratio, the adapting includes increasing a voltage provided by the electrodes and decreasing a duration of the at least one the rest time to a predetermined minimum rest-time value.

In some embodiments, when each of the first and the second time ratio is less than the predetermined threshold ratio, the adapting includes increasing a duration of each rest-time, and when each of the first and the second time ratio is equal to or greater than the predetermined threshold ratio, the adapting includes increasing a voltage provided by the electrodes and decreasing a duration of each rest time to a predetermined minimum rest-time value.

In some embodiments, the adapting further includes adapting a phase width of at least one the positive phase or at least one the negative phase. In some embodiments, the adapting a phase width includes adapting a phase width of each positive phase and each negative phase.

In some embodiments, a duration of the positive phase train is different from a duration of the negative phase train. In some embodiments, the cumulative duration of the positive phases is different from the cumulative duration of the negative phases. In some embodiments, the cumulative duration of the rest times between the positive phases in the positive phase train is different from the cumulative duration of the rest times between the negative phases in the negative phase train.

In some embodiments, a number of the positive phases in the positive phase train is different from a number of the negative phases in the negative phase train. In some embodiments, a duration of the positive phase train is equal to a duration of the negative phase train. In some embodiments, the cumulative duration of the positive phases is equal to the cumulative duration of the negative phases.

In some embodiments, the cumulative duration of the rest times between the positive phases in the positive phase train is equal to the cumulative duration of the rest times between the negative phases in the negative phase train.

In some embodiments, a number of the positive phases in the positive phase train is equal to a number of the negative phases in the negative phase train.

In some embodiments, the region of the head is a hair covered region of the head. In some embodiments, the engaging includes engaging the electrodes at the hair covered region of the head. In some embodiments, the region of the head includes a cephalic nerve, such that the electrical stimulation is delivered to the cephalic nerve in the region of the head.

In some embodiments, the engaging includes mounting a headset, including the at least two electrodes and the electronic circuit, on the head of the user such that the at least two electrodes engage the surface of the scalp.

In some embodiments, the predetermined threshold ratio is in the range of 0.4-1.2, 0.5-1, or 0.55-0.75. In some embodiments, the predetermined threshold ratio is 0.6.

In some embodiments, a duration of each rest time in the positive phase train and in the negative phase train at least equals a minimum rest time duration. In some embodiments, the minimum rest time duration is 5 µsec.

In some embodiments, a phase width of each of the positive phases and of each of the negative phases is not greater than a maximal phase width. In some embodiments, the maximal phase width is at most 600 µsec, at most 400 µsec, at most 200 µsec, at most 100 µsec, or at most 50 µsec.

In some embodiments, the monitoring is carried out by the electrodes.

In some embodiments, the monitoring is carried out by at least one sensor external to the electrodes, the sensor engaging the skin of the scalp of the user and being functionally associated with the electronic circuit.

In some embodiments, the monitoring includes monitoring a provided waveform for each of the positive and the negative phases, to identify, for each positive and the negative phase, whether the provided waveform is identical to an intended waveform, and wherein the reduction of charge is identified if the provided waveform is not identical to the intended waveform.

In some embodiments, the adapting includes adapting at least one of the first time ratio and the second time ratio. In some embodiments, the adapting includes adapting the first time ratio and the second time ratio.

In some embodiments, the adapting further includes changing a number of the positive phases in the positive phase train. In some embodiments, the adapting further includes changing a number of the negative phases in the negative phase train. In some embodiments, the adapting further includes changing an amplitude of at least one of the positive phases and the negative phases.

In some embodiments, the monitoring further includes the electronic circuit measuring impedance in the electrodes, and wherein the adapting takes place upon identification of the impedance exceeding an impedance threshold.

In some embodiments, the monitoring further includes monitoring a voltage delivered by the electrodes, and wherein the adapting takes place upon identification of the voltage reaching an upper voltage threshold. In some embodiments, the upper voltage threshold is the compliance voltage.

In some embodiments, the method further includes, following the monitoring showing that the predetermined amount of charge has been provided by each of the positive and the negative phases and completion of the step (e), additionally monitoring the amount of charge delivered by the positive and the negative phases, to identify a change in the charge delivered by the positive and the negative phases.

In some embodiments, the change is indicative of a change in conditions in which the positive and the negative phases are provided. In some embodiments, the change in the conditions includes a change in impedance measured between the at least two electrodes.

In some embodiments, the additionally monitoring is carried out periodically.

In some embodiments, the additionally monitoring is carried out intermittently.

In some embodiments, the additionally monitoring is carried out in response to receipt of an indication from the user. In some embodiments, the indication includes an indication of discomfort or pain.

In some embodiments, the additionally monitoring is carried out in response to receipt of a signal from a humidity sensor indicating a change in humidity in an area adjacent the electrodes.

In some embodiments, the additionally monitoring is carried out in response to receipt of a signal from a temperature sensor indicating a change in temperature in an area adjacent the electrodes.

In some embodiments, the additionally monitoring is carried out in response to receipt of a signal from an accelerometer indicating a change in at least one of a position of the user, a position of the electrodes, and pressure applied to the electrodes.

In some embodiments, the additionally monitoring is carried out in response to receipt of a signal from a pressure sensor indicating a change in pressure applied to the electrodes.

In some embodiments, the method further includes, following identification of the change in conditions by the additionally monitoring, repeating the steps (d) and (e) of the method.

In some embodiments, the method further includes, following at least one of the first time ratio and the second time ratio reaching the predetermined threshold ratio and the voltage reaching the predetermined voltage threshold, terminating application of the electrical stimulation, and notifying the user that treatment has been terminated.

In some embodiments, the method further includes, following step (a) and prior to step (b):

delivering via the engaged electrodes a balanced singular constant-current pulse including a positive phase immediately followed by a negative phase, the positive and negative phases intended to provide a predetermined amount of charge to the head of the user; and identifying that impedance in the electronic circuit during delivery of the singular pulse has reached a predetermined impedance threshold.

In some embodiments, the method further includes, following step (a) and prior to step (b):

delivering via the engaged electrodes a balanced singular constant-current pulse including a positive phase immediately followed by a negative phase, the positive and negative phases intended to provide a predetermined amount of charge to the head of the user; and identifying that a voltage required to deliver the singular constant current pulse has reached an upper voltage threshold.

In some embodiments, the upper voltage threshold is the compliance voltage of the electronic circuit.

According to some teachings of the present invention there is provided a head mounted device including:

at least a pair of electrodes, configured, when the head mounted device is donned, to engage the scalp of the user and to deliver to the scalp of the user a balanced pulse including a positive phase train including a streak of constant current positive phases separated by rest times, the positive phase train immediately followed by a negative phase train including a streak of constant current negative phases separated by rest times, each of the positive phases and the negative phases intended to provide a predetermined amount of charge to the head of the user, wherein:

each of a first time ratio, between a cumulative duration of the rest times between the positive phases in the positive phase train and a cumulative duration of the positive phases, and a second time ratio, between a cumulative duration of the rest times between the negative phases in the negative phase train and a cumulative duration of the negative phases is smaller than a predetermined threshold ratio;

the positive phases and the negative phases have a common phase width $w_i$; and the rest times between immediate successor phases in the positive phase train and in the negative phase train having a common rest-time value $rt^i$;

at least one sensor adapted, when the head mounted device is donned by the user and during transmission of the pulse, to engage the skin of the scalp of the user and to monitor an amount of charge delivered by the positive phases and the negative phases;

an electronic circuit, functionally associated with the at least two electrodes and having a compliance voltage; and a processing unit, functionally associated with the electrodes to provide instructions thereto and with the at least one sensor to receive input therefrom, the processing unit programmed to:

(a) receive input from the at least one sensor, (b) identify in the received input a reduction of charge delivered by one or more of the positive and the negative phases;

(c) upon identification of a reduction, to provide input to the electrodes causing adaptation of the common rest time value; and (d) repeat steps (a)-(c) until:
the predetermined amount of charge has been provided by each of the positive and the negative phases; or
at least one of the first time ratio and the second time ratio reaches the predetermined threshold ratio and a voltage of the balanced pulse reaches a predetermined voltage threshold.

In some embodiments, the processing unit is further programmed:

when each of the first and the second time ratio is less than the predetermined threshold ratio, to provide input to the electrodes causing the common rest-time value to increase; and when each of the first and the second time ratio is equal to or greater than the predetermined threshold ratio, to provide input to the electrodes causing a voltage provided by the electrodes to increase and the common rest time value to decrease to a predetermined minimum rest-time value.

In some embodiments, the processing unit is further configured to provide input to the electrodes causing adaptation of the common phase width.

According to some teachings of the present invention there is provided a head mounted device including:

at least a pair of electrodes, configured, when the head mounted device is donned, to engage the scalp of the user and to deliver to the scalp of the user a balanced pulse including a positive phase train including a streak of constant current positive phases separated by rest times, the positive phase train immediately followed by a negative phase train including a streak of constant current negative phases separated by rest times, each of the positive phases and the negative phases intended to provide a predetermined amount of charge to the head of the user, wherein each of a first time ratio, between a cumulative duration of the rest times between the positive phases in the positive phase train and a cumulative duration of the positive phases, and a second time ratio, between a cumulative duration of the rest times between the negative phases in the negative phase train and a cumulative duration of the negative phases is smaller than a predetermined threshold ratio;

at least one sensor adapted, when the head mounted device is donned by the user and during transmission of the pulse, to engage the skin of the scalp and to monitor an amount of charge delivered by the positive phases and the negative phases;

an electronic circuit, functionally associated with the at least two electrodes and having a compliance voltage; and a processing unit, functionally associated with the electrodes to provide instructions thereto and with the at least one sensor to receive input therefrom, the processing unit programmed to:

(a) receive input from the at least one sensor, (b) identify in the received input a reduction of charge delivered by one or more of the positive and the negative phases;

(c) upon identification of a reduction, to provide input to the electrodes causing adaptation of at least one the rest time in at least one of the positive phase train and the negative phase train; and (d) repeat steps (a)-(c) until:
the predetermined amount of charge has been provided by each of the positive and the negative phases; or
at least one of the first time ratio and the second time ratio reaches the predetermined threshold ratio and a voltage of the balanced pulse reaches a predetermined voltage threshold.

In some embodiments, the electrodes are configured to deliver a pulse wherein the positive phases in the positive phase train have a common phase width $w_p$. In some embodiments, the electrodes are configured to deliver a pulse wherein the negative phases in the negative phase train have a common phase width $w_n$. In some embodiments, the electrodes are configured to deliver a pulse wherein the positive phases in the positive phase train and the negative phases in the negative phase train have a common phase width $w_i$.

In some embodiments, the electrodes are configured to deliver a pulse wherein the rest times between immediate successor phases in the positive phase train have a common rest-time value $rt^p$. In some embodiments, the electrodes are configured to deliver a pulse wherein the rest times between immediate successor phases in the negative phase train have a common rest-time value $rt^n$. In some embodiments, the electrodes are configured to deliver a pulse wherein the rest times between immediate successor phases in the positive phase train and in the negative phase train have a common rest-time value $rt^t$.

In some embodiments, the processing unit is further programmed:

when each of the first and the second time ratio is less than the predetermined threshold ratio, to provide input to the electrodes causing a duration of the at least one the rest-time to be increased; and when each of the first and the second time ratio is equal to or greater than the predetermined threshold ratio, to provide input to the electrodes causing a voltage provided by the electrodes to be increased and a duration of the at least one the rest time to be decreased to a predetermined minimum rest-time value.

In some embodiments, the processing unit is further programmed:

when each of the first and the second time ratio is less than the predetermined threshold ratio, to provide input to the electrodes causing a duration of each rest-time to be increased; and when each of the first and the second time ratio is equal to or greater than the predetermined threshold ratio, to provide input to the electrodes causing a voltage provided by the electrodes to be increased and a duration of each rest time to be decreased to a predetermined minimum rest-time value.

In some embodiments, the processing unit is further programmed to provide input to the electrodes causing adaptation to a phase width of at least one the positive phase or at least one the negative phase. In some embodiments, the processing unit is further programmed to provide input to the electrodes causing adaptation to a phase width of each positive phase and each negative phase.

In some embodiments, the electrodes are configured to deliver a pulse wherein a duration of the positive phase train is different from a duration of the negative phase train. In some embodiments, the electrodes are configured to deliver a pulse wherein the cumulative duration of the positive phases is different from the cumulative duration of the negative phases. In some embodiments, the electrodes are configured to deliver a pulse wherein the cumulative duration of the rest times between the positive phases in the positive phase train is different from the cumulative duration of the rest times between the negative phases in the negative phase train.

In some embodiments, the electrodes are configured to deliver a pulse wherein a number of the positive phases in the positive phase train is different from a number of the negative phases in the negative phase train. In some embodiments, the electrodes are configured to deliver a pulse wherein a duration of the positive phase train is equal to a duration of the negative phase train. In some embodiments, the electrodes are configured to deliver a pulse wherein the cumulative duration of the positive phases is equal to the cumulative duration of the negative phases.

In some embodiments, the electrodes are configured to deliver a pulse wherein the cumulative duration of the rest times between the positive phases in the positive phase train is equal to the cumulative duration of the rest times between the negative phases in the negative phase train. In some embodiments, the electrodes are configured to deliver a pulse wherein a number of the positive phases in the positive phase train is equal to a number of the negative phases in the negative phase train.

In some embodiments, the device further includes a body member adapted to be donned on the head of a user, wherein the electrodes and the sensor are mounted onto an inner surface of the body member.

In some embodiments, the region of the head is a hair covered region of the head. In some embodiments, the electrodes are configured, when the head mounted device is donned, to engage the hair covered region of the head. In some embodiments, the region of the head includes a cephalic nerve, such that the electrodes are configured to deliver the electrical stimulation to the cephalic nerve in the region of the head.

In some embodiments, the predetermined threshold ratio is in the range of 0.4-1.2, 0.5-1, or 0.55-0.75. In some embodiments, the predetermined threshold ratio is 0.6.

In some embodiments, the electrodes are configured to deliver a pulse wherein a duration of each rest time in the positive phase train and in the negative phase train is at least equal to a minimum rest time duration. In some embodiments, the minimum rest time duration is 5 μsec.

In some embodiments, the electrodes are configured to deliver a pulse wherein a phase width of each of the positive phases and of each of the negative phases is not greater than a maximal phase width. In some embodiments, the maximal phase width is at most 600 μsec, at most 400 μsec, at most 200 μsec, at most 100 μsec or at most 50 μsec.

In some embodiments, the at least one sensor is at least one of the electrodes.

In some embodiments, the at least one sensor is external to the electrodes and is functionally associated with the electronic circuit.

In some embodiments, the at least one sensor is configured to monitor a provided waveform of each of the positive and the negative phases, and wherein the processing unit is configured to identify, for each positive and the negative phase, whether the provided waveform is identical to an intended waveform, and to identify the reduction of charge if the provided waveform is not identical to the intended waveform.

In some embodiments, the processing unit is configured to provide to the electrodes instruction for adapting at least one of the first time ratio and the second time ratio. In some embodiments, the processing unit is configured to provide to the electrodes instruction for adapting the first time ratio and the second time ratio.

In some embodiments, the processing unit is configured to provide to the electrodes instructions for changing a number of the positive phases in the positive phase train. In some embodiments, the processing unit is configured to provide to the electrodes instructions for changing a number of the negative phases in the negative phase train. In some embodiments, the processing unit is configured to provide to the electrodes instructions for changing an amplitude of at least one of the positive phases and the negative phases.

In some embodiments, the at least one sensor is configured to monitor impedance in the electronic circuit, and the processing unit is configured to identify the impedance exceeding an impedance threshold.

In some embodiments, the at least one sensor is configured to monitor a voltage delivered by the electrodes, and the processing unit is configured to identify the voltage reaching an upper voltage threshold. In some embodiments, the upper voltage threshold is the compliance voltage.

In some embodiments, following the processing unit identifying that the predetermined amount of charge has been provided by each of the positive and the negative phases and completion of the step (d), the processing unit is configured to receive additional input at least from the at least one sensor and to identify at least one of a change in the charge delivered by the positive and the negative phases and a change in conditions in which the positive and the negative phases are provided.

In some embodiments, the at least one sensor is configured to measure a change in impedance between the at least two electrodes and to provide the measurement to the processing unit as the additional input.

In some embodiments, the device further includes a timer functionally associated with at least one of the processing unit and the at least one sensor, and configured to trigger the at least one sensor to provide the additional input periodically.

In some embodiments, the device further includes a user interface functionally associated with the processing unit, wherein the additional input includes input provided by the user via the user interface. In some embodiments, the additional input includes an indication of discomfort or pain provided by the user.

In some embodiments, the device further includes a humidity sensor functionally associated with the processing unit and configured to sense humidity in an area adjacent to the electrodes, and wherein the additional input includes a signal provided from the humidity sensor to the processing unit, the signal indicating a change in humidity in an area adjacent the electrodes.

In some embodiments, the device further includes a temperature sensor functionally associated with the processing unit and configured to sense a temperature in an area adjacent to the electrodes, and wherein the additional input includes a signal provided from the temperature sensor to the processing unit, the signal indicating a change in temperature in an area adjacent the electrodes.

In some embodiments, the device further includes an accelerometer functionally associated with the processing unit and configured to sense at least one of a position of the user and a position of the electrodes, and wherein the additional input includes a signal provided from the accelerometer to the processing unit, the signal indicating a change in at least one of a position of the user, a position of the electrodes, and pressure applied to the electrodes.

In some embodiments, the device further includes a pressure sensor functionally associated with the processing unit and configured to sense pressure applied to the electrodes, and wherein the additional input includes a signal provided from the pressure sensor to the processing unit, the signal indicating a change in pressure applied to the electrodes.

In some embodiments, the processing unit is further configured, following identification of the change in conditions, to repeat the steps (c) and (d).

In some embodiments, the device further includes a user notification module functionally associated with the processing unit and wherein, following at least one of the first time ratio and the second time ratio reaching the predetermined threshold ratio and the voltage reaching the predetermined voltage threshold, the processing unit terminates application of the electrical stimulation, and the user notification module notifies the user that treatment has been terminated.

In some embodiments, the electrodes are configured to deliver, prior to delivery of the positive phase train and the negative phase train a balanced singular constant-current pulse including a positive phase immediately followed by a negative phase, the positive and negative phases intended to provide a predetermined amount of charge to the head of the user, and the processing unit is configured, prior to delivery of the positive phase train and the negative phase train, to identify that impedance in the electronic circuit during delivery of the singular pulse has reached a predetermined impedance threshold.

In some embodiments, the electrodes are configured to deliver, prior to delivery of the positive phase train and the negative phase train, a balanced singular constant-current pulse including a positive phase immediately followed by a negative phase, the positive and negative phases intended to provide a predetermined amount of charge to the head of the user, and the processing unit is configured to identify, prior to delivery of the positive phase train and the negative phase train that a voltage required to deliver the singular constant current pulse has reached the upper voltage threshold, which, in some embodiments, is the compliance voltage of the electronic circuit.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like functionalities, but not necessarily identical elements.

In the drawings:

FIGS. 4A, 4B, and 4C are schematic illustrations of a pulse transmitted in accordance with an embodiment of the teachings herein when experiencing different impedances, wherein FIG. 4A illustrates the current provided by the pulse under standard impedance conditions, FIG. 4B illustrates the current provided by the pulse under high impedance conditions, and FIG. 4C illustrates the voltage on the electrodes providing the pulse under high impedance conditions;

FIGS. 5A, 5B, and 5C are schematic illustrations of a pulse including a phase train of positive phases and a phase train of negative phases in accordance an embodiment of the teachings herein, each of the Figures corresponding to a different stage of the method of claim 2, wherein FIG. 5A illustrates a phase train pulse which provides sufficient charge, FIG. 5B illustrates the phase train pulse similar to that of FIG. 5A but not providing sufficient charge, and FIG. 5C illustrates a second phase train pulse providing sufficient charge and having longer rest times between phases;

DETAILED DESCRIPTION

Systems and methods are described herein that apply electrical stimulation to the head region, for stimulation of peripheral and/or cranial nerves, transcranial stimulation of brain regions, and sensing of body parameters, while monitoring the tissue and adapting the electrical stimulation signal to the user's characteristics and to changes over time. The systems and methods ensure effective electrical stimulation while avoiding damage to scalp tissue as well as discomfort to the user, and operate in a safe and robust fashion.

The inventive methods may be applied using a head mounted construction serving as a platform for applying electrical stimulation in accordance with the inventive methods to treat various conditions such as migraine and tension headaches, cluster headaches, fibromyalgia, depression, post-traumatic stress disorder (PTSD), anxiety, obsessive compulsive disorder (OCD), insomnia, epilepsy, attention deficit hyperactivity disorder (ADHD), Parkinson's disease, Alzheimer's disease, obesity, multiple sclerosis, traumatic brain injury (TBI) and stroke.

The quality of contact between the stimulation electrodes and the scalp is a fundamental aspect in the provision of neurostimulation. Given the fact that such contact, and the resulting conductivity are not always optimal, the inventors have developed a method for compensating for reduced conductivity or increased impedance, for example due to presence of hair, lack of humidity, and the like, while maintaining the user's skin integrity, comfort, and ensuring proper neurostimulation.

Electrical stimulation of a pure sensory nerve elicits radiation of a paresthesia sensation along the distribution of the nerve. The existence of paresthesia at the relevant anatomical area is an indication that effective nerve excitation is taking place. Conversely, absence of paresthesia along the distribution of the nerve during stimulation may reflect an inability to reach effective nerve excitation due to inappropriate stimulation parameters such as excessively low intensity, insufficient current density or charge, or due to other reasons such as inappropriate electrode location or high impedance.

Eliciting paresthesia is an important factor also in the treatment of pain. According to the "Gate-control theory", activation of large sensory $A\beta$ nerve fibers, which is indicated by the paresthesia sensation, leads to inhibition of small diameter nociceptive $A\delta$ and C fibers and thereby impedes the sensation of pain. As such, it is desirable to maintain the user's sensation of paresthesia during neurostimulation treatment. Several aspects of the present invention relate to methods and techniques that are aimed at ensuring that the electrical current is properly and effectively delivered from the electrodes to the target tissues while keeping the voltage applied to the tissue sufficiently low.

Figure 1A:
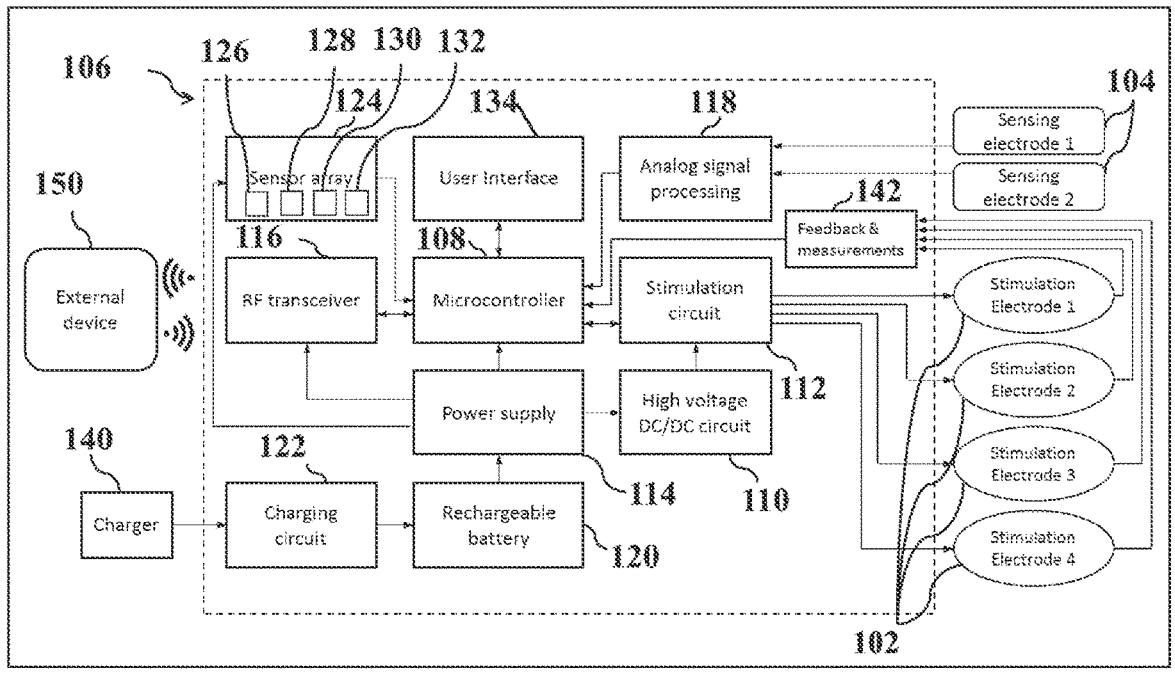
FIG. 1A is a schematic block diagram of an embodiment of an inventive system for neurostimulation according to an embodiment of the teachings herein.

Reference is now made to FIG. 1A, which is a schematic block diagram of an embodiment of an inventive system for neurostimulation according to an embodiment of the teachings herein.

As seen, a system 100 for neurostimulation may include at least two stimulating electrodes 102, and in some embodiments may further include at least two sensing electrodes 104, both the electrodes 102 and 104 functionally associated with an electronic circuit 106. The stimulating electrodes 102 are adapted to engage the skin of the user's scalp so as to deliver current thereto as described hereinbelow. In some embodiments, one or more of sensing electrodes 104 may be adapted to engage the skin of the user, and may be configured to sense at least one electrical parameter of a body portion of the user, such as, for example, electroencephalogram (EEG), skin conductance response (SCR), impedance plethysmograph (IPG), electromyograph (EMG), and the like.

According to features of the teachings herein, system 100, and specifically the electronic circuit 106, may be suited for applying transcranial electrical stimulation using suitable methods such as Transcranial Direct Current Stimulation (tDCS), Transcranial Alternating Current Stimulation (tACS), and Transcranial Random Noise Stimulation (tRNS).

As seen, the electronic circuit 106 may include any one or more of a microcontroller 108, a high voltage circuit 110, a stimulation circuit 112, an internal power supply 114, a radio-frequency (RF) transceiver 116, an analog signal processing circuit 118, a rechargeable battery 120 electrically associated with a charging circuit 122, a sensor array 124 including one or more of an accelerometer 126, a temperature sensor 128, a pressure sensor 130, and a humidity sensor 132, and a user interface 134.

In some embodiments, the electronic circuit 106 may be electrically associated with and powered by rechargeable battery 120 that is electrically connected to internal power supply 114. In some embodiments, the internal power supply 114 provides power to high voltage circuit 110, which in turn is electrically connected to stimulation circuit 112. The charging circuit 122 is electrically associated with rechargeable battery 120, and may interface with an external power supply, such as a charger 140. The high voltage circuit 110 provides to stimulation circuit 112 current with voltage in the range of 1 to 150 V.

In some embodiments, the stimulation circuit 112 receives information and/or commands from the microcontroller 108. The stimulation circuit 112 is configured to provide electrical stimulation pulses to the user's nerve tissues via the stimulation electrodes 102.

The stimulation circuit 112 may be configured to produce biphasic, charged balanced electrical pulses, mono-phasic electrical pulses, and/or direct current stimulation.

According to still further features of the described preferred embodiments, the stimulation circuit 112 may be configured to produce electrical stimulation within an intensity range of 0-60 mA, 0-40 mA, 0-20 m, or 0-15 mA.

According to still further features of the described preferred embodiments, the stimulation circuit 112 may be configured to produce stimulation pulses with a duration of 10-1000 μsec, 50-600 μsec, 100-500 μsec.

According to still further features of the described preferred embodiments, the stimulation circuit 112 may be configured to produce stimulation pulses at a frequency of 1-20,000 Hz, 1-10,000 Hz, 1-500 Hz, 10-300 Hz, 10-250 Hz, 20-180 Hz, 30-180 Hz or 40-100 Hz.

In some embodiments, electronic circuit 106 may include two or more high voltage circuits (not shown) similar to circuit 112, each high voltage circuit providing current at a voltage of 1-150V, 1-120V, 1-100V, to at least two of stimulation electrodes 102. In some embodiments, electronic circuit 106 may include at least two isolated output channels (not shown), each output channel providing output to at least two of stimulation electrodes 102.

In some embodiments, the electronic circuit 106 also includes a feedback & measurements circuit 142, which collects voltage or current level information from the stimulation electrodes 102, and provides the collected information to the microcontroller 108. The microcontroller 108 uses the provided feedback to monitor and control the voltage and current levels in stimulation electrodes 102 via stimulation circuit 112 in accordance with the method disclosed herein with respect to FIGS. 2 and 3. In some embodiments, the microcontroller 108 may alert the user, for example by providing an audible or tactile indication, or may halt the provision of current for stimulation in the case of an emergency or of incorrect function of the system, as described hereinbelow with reference to FIG. 2.

In some embodiments, the microcontroller 108 may instruct the stimulation circuit 112 to output electrical current in various patterns and/or for various periods of time, and/or may instruct the stimulation circuit 112 with regards to various stimulation parameters, such as the current amplitude, pulse frequency, phase duration, and amplitude of the current output by the stimulation circuit, as described hereinbelow with reference to FIG. 2.

In some embodiments, the microcontroller 108 may instruct the stimulation circuit 112 to provide an output signal having a different pattern for each of a plurality of activated pairs of electrodes. For example, the stimulation circuit 112 may stimulate one pair of electrodes at a pulse frequency of 50 Hz and a phase duration of 300 μsec and another pair of electrodes at a pulse frequency of 100 Hz and a phase duration of 200 μsec. In some embodiments, at any given time the microcontroller 108 may activate only one pair of electrodes, may activate a combination of electrodes, and/or may activate several electrodes simultaneously, sequentially, or alternately.

In some embodiments, some electrodes 102 may provide as output an alternating current signal, whereas other electrodes 102 may provide as output a direct current. In some embodiments, at least two electrodes 102 may alternate the type of current provided as output between alternating current and direct current.

In some embodiments, during direct current stimulation in which excitation of a certain region of the brain is determined based on the polarity of an electrode which is positioned above that region of the brain, at least one electrode 102 may be assigned by the microcontroller 108 to be the anode, or positively charged electrode, and at least one other electrode 102 may be assigned to be the cathode, or negatively charged electrode.

In some embodiments, stimulation patterns determined by or assigned by the microcontroller 108 as described hereinbelow with reference to FIG. 2, as well as feedback data received from electrodes 102 and/or from sensing electrodes 104 may be stored in the microcontroller 108 or in a volatile or non-volatile memory (not shown) associated therewith. In some embodiments, the stored stimulation patterns may be used to create a personalized neurostimulation protocol for the user, as described hereinbelow with reference to FIG. 3.

In some embodiments, electronic circuit 106 may be configured to receive analog signal input, such as electroencephalogram (EEG) signals, skin conductance response (SCR) signals, impedance plethysmograph (IPG) signals, electromyograph (EMG) signals, or other bio-signals, from one or more sensors, such as sensing electrodes 104, which bio-signals may be indicative of the impedance of the tissue receiving the neurostimulation signal, the charge provided to the tissue, or the like. The analog signal input received from sensing electrodes 104 may be processed by analog signal processing circuit 118, and may be transferred therefrom to microcontroller 108. In some embodiments, electronic circuit 106 may be configured to receive digital, analog, or other input from additional sensors adapted to sense the vicinity of the user or characteristics thereof. In some embodiments, one or more stimulation parameters may be altered by the microcontroller 108 due to inputs received from one or more of the additional sensors, as described hereinbelow.

In some embodiments, accelerometer 126, or any other suitable orientation sensor, may be configured to sense the angular position of the user's head or of the system 100 (and particularly portions thereof engaging the user's head), and thereby may enable microcontroller 108 to identify a change in the user's and/or system's conditions and to adjust or adapt the pulse provided by stimulating electrodes 102. For example, a change in the position of the user may result in a change in the pressure applied to the electrodes, thus changing how close the electrodes are to the user's skin and consequently changing the impedance in the system and requiring adaptation of the pulse applied to the tissue via the electrodes, as described hereinbelow.

In some embodiments, temperature sensor 128 may be configured to sense a temperature in the vicinity of the system 100 or of the stimulating electrodes 102, and thereby may enable microcontroller 108 to identify a change in the user's and/or system's conditions and to adjust or adapt the pulse provided by stimulating electrodes 102. For example, an increase in the temperature in the vicinity of the user or of the electrodes 102 may result in more rapid dehydration of the electrodes or of conducting material applied thereto, thus increasing the impedance in the system and requiring adaptation of the pulse applied to the tissue via the electrodes, as described hereinbelow.

In some embodiments, pressure sensor 130 may be configured to sense pressure applied to the user's head in the vicinity of electrodes 102 or pressure applied directly to electrodes 102, and thereby may enable microcontroller 108 to identify a change in the user's and/or system's conditions and to adjust or adapt the pulse provided by stimulating electrodes 102. For example, an increase in the amount of pressure applied to electrodes 102 pushing them towards the user's scalp is expected to reduce the distance between the electrodes and the scalp, and in some cases the distance between the electrode and the target nerve, thereby reducing the impedance in the system and requiring, or allowing, adaptation of the pulse applied to the tissue via the electrodes, as described hereinbelow.

In some embodiments, humidity sensor 132 may be configured to sense a humidity or moisture level in the vicinity of the system 100 or of the stimulating electrodes 102, and thereby may enable microcontroller 108 to identify a change in the user's and/or system's conditions and to adjust or adapt the pulse provided by stimulating electrodes 102. For example, a decrease in the sensed humidity in the vicinity of the electrodes 102 may be indicative of dehydration of the electrodes or of conducting material applied thereto, thus increasing the impedance in the system and requiring adaptation of the pulse applied to the tissue via the electrodes, as described hereinbelow.

In some embodiments, user interface 134 may be configured to receive from the user an indication of the sensation the user is feeling, such as an indication of pain, an indication of discomfort, or an indication of decreased, or no, paresthesia. Such an indication from the user of a change in the sensation the user feels may enable microcontroller 108 to adjust or adapt the pulse provided by stimulating electrodes 102.

In some embodiments, RF transceiver 116 may enable the microcontroller 108 to communicate with an interface of an external device 150, such as a mobile phone, a tablet, a computer, or a cloud based database, by way of radio frequency. The RF transceiver 116 may transmit digital information to and may receive digital information from the microcontroller 108, for example for personalization of the neurostimulation provided by system 100, as described hereinbelow with reference to FIG. 3.

The interface of device 150 may comprise a software application that may be downloadable from a readily accessible resource, such as from the Internet. The interface may provide to a user thereof an indication, for example by way of a display, of the status of the system 100, including, for example, information relating to active stimulation channels, stimulation intensity, active program, treatment time, battery status, and RF communication status, as well as various alerts such as alerts relating to electrode contact quality and to proper or improper system alignment on the head. Additionally, the interface may provide to the user, for example by way of a display, usage logs and/or reports, such as information relating to daily stimulation time, stimulation parameters which were used during stimulation, and treatment programs which were used. The interface may also display, or otherwise provide, to the user raw or processed information received from sensors included in or associated with the headset.

In some embodiments, the system may be controlled remotely via the interface of external device 150. For example, the external interface may enable a user thereof to activate or turn off the system, start or pause stimulation, adjust the stimulation intensity for one or more channels, and select a treatment program. In some embodiments, information collected by the microprocessor 108 may be transmitted, via the external interface, to a remote location, such as a cloud based portal, where the information may be stored or may be analyzed and/or monitored, for example as described hereinbelow with reference to FIG. 3.

Figure 1B:
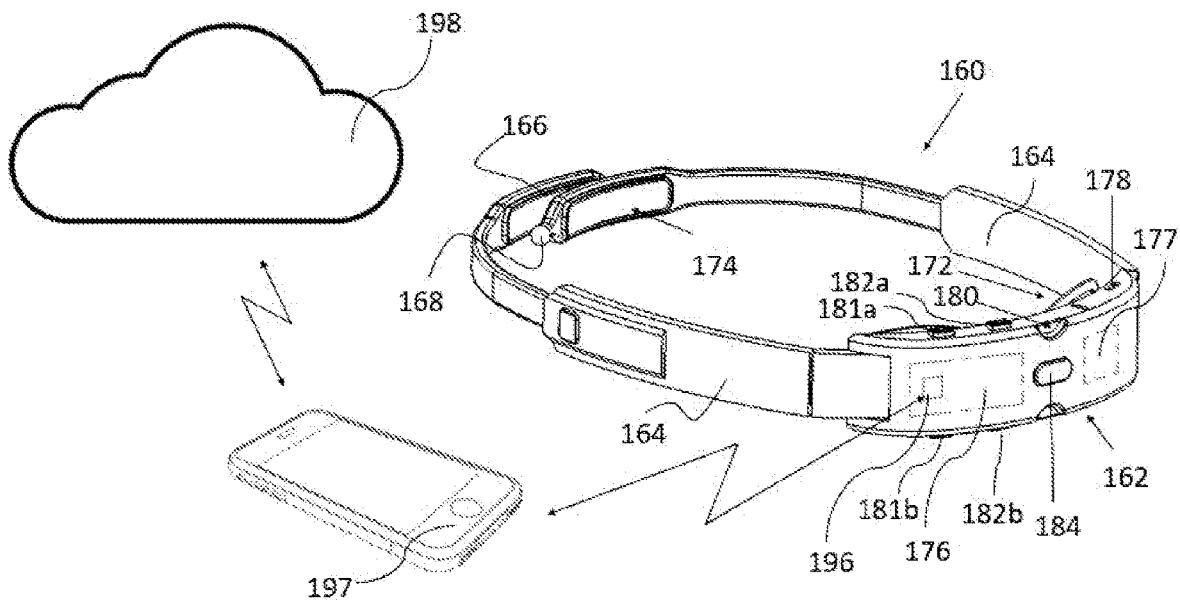
FIG. 1B is a perspective view schematic illustration of an embodiment of the inventive system of FIG. 1A in the form of a headset communicating with external data sources according to the teachings herein.

Reference is now made to FIG. 1B, which is a perspective view schematic illustration of an embodiment of the inventive system 100 of FIG. 1A in the form of a headset communicating with external data sources according to the teachings herein.

As seen, a headset 160 may implement the system 100 of FIG. 1A, and may be configured to include an anterior member 162 connected to a pair of flexible arm members 164, which may also be called interim members, each terminating in a posterior member 166. Anterior member 162, flexible arm members 164, and posterior members 166 together form the headset body.

In some embodiments, each posterior member 166 comprises a terminal portion having a tapered end terminating in a closure mechanism 168.

Anterior member 162 may be configured to contain, on an interior surface thereof, one or more anterior electrode systems 172, and each of posterior members 166 may be configured to contain, on an interior surface thereof, one or more posterior electrode systems 174, electrode systems 172 and 174 implementing or being similar to stimulating electrodes 102 of FIG. 1A. Each of electrode systems 172 and 174 may comprise an electrode base and a disposable electrode unit, which may, in some embodiments, be structured and functional as described in patent application publications US2015/0374971, AU2015227382, EP2981326, CN105188835, WO2014/141213 and IL241026, all entitled HEADSET FOR TREATMENT AND ASSESSMENT OF MEDICAL CONDITIONS, and WO2016/042499 entitled HEADSET FOR NEUROSTIMULATION AND SENSING OF BODY PARAMETERS filed by the present inventors, which are incorporated by reference as if fully set forth herein.

In some embodiments, electrode systems 172 may comprise anterior electrodes adapted to be located at the supraorbital region of the head over the trigeminal nerve branches for stimulation thereof, or may be electrodes suitable for transcranial stimulation of the frontal and prefrontal region of the brain.

In some embodiments, electrode systems 174 may comprise posterior electrodes adapted to be located at the occipital region of the head over the occipital nerve branches for stimulation thereof, or may be electrodes suitable for transcranial stimulation of the occipital region of the brain.

In some embodiments, one or more of electrode systems 172 and 174 may comprise sensing electrodes similar to sensing electrodes 104 of FIG. 1A, configured to sense at least one electrical parameter of a body portion of said user, such as, for example, electroencephalogram (EEG), skin conductance response (SCR), impedance plethysmograph (IPG), electromyograph (EMG), and the like.

It will be appreciated that headset 160 may include additional electrodes having similar structure and/or functionality to those of electrode systems 172 and 174. It is further appreciated that electrode systems 172 and/or 174 may be obviated, or moved to other locations on headset 160, as suitable for stimulating specific nerves or nerve sets, specific brain regions, or for sensing specific parameters. For example, electrode systems 174 may be moved to be along the flexible arm members 164. As another example, the headset 160 may include only a single pair of electrode systems located on arm members 164, which electrodes may be configured to be positioned, when the headset is donned, under the hair, while electrode systems 172 and 174 may be obviated.

Anterior member 162 may be configured to contain an electronic circuit 176, similar to electronic circuit 106 of FIG. 1A, which may be configured to be electrically coupled by conductive wires (not shown) to a power source 177, such as a battery similar to battery 120 of FIG. 1A, and to electrodes systems 172 and 174. In some embodiments, at least a portion of the conductive wires extends to posterior electrode systems 174 via arm members 164.

In some embodiments, the electronic circuit 176 and/or the battery 177 may be external to headset 160, and/or may communicate remotely with headset 160.

As discussed hereinabove with reference to FIG. 1A, the electronic circuit 176 may include a stimulation circuit, a microprocessor, a charging circuit and a user interface.

In some embodiments, headset 160 may be configured to connect to an external electronic circuit and/or stimulation circuit, and thereby to transfer electrical current from an external stimulator to the electrode systems 172 and/or 174. In some embodiments, headset 160 may be configured to connect to at least one external electrode that may be located at various areas of the body. In some embodiments, headset 160 may be configured to connect to an external electronic circuit and processor in order to transfer signals from sensors disposed on the headset 160 to the external processor.

In some embodiments, battery 177 may be disposed within anterior member 162, and may be recharged by plugging a charger into charging port 178 located, according to certain embodiments, on anterior member 162.

Anterior member 162 may also be configured to include, on an external surface thereof, user controls and interface 180, which may be similar to user interface 134 of FIG. 1A. That said, in some embodiments, other portions of headset 160, such as posterior members 166 or arms 164, may be configured to include user interface 180. In some embodiments, user interface 180, or an additional user interface (not shown) may be external to headset 160 and may communicate with headset 160 remotely, using wired or wireless communication, as explained hereinabove with reference to FIG. 1A.

Electronic circuit 176 and user interface 180 may be configured to control and/or activate electrodes included in headset 160. In some embodiments, user interface 180 is configured to control and/or activate at least two, and in some embodiments more than two, pairs of electrodes. As such, in some embodiments, the stimulation circuit and/or user interface 180 are configured to enable activation of a specific electrode or of a specific pair, or channel, of electrodes, as well as adjustment of the intensity of current supplied by the activated electrodes or of other stimulation parameters of the activated electrodes and provision of user indications such as a user indication of pain, a user indication of discomfort, or a user indication of reduced or increased paresthesia. In some embodiments, any subset of the electrodes may be activated simultaneously, and in some embodiments specific subsets are predefined, for example during manufacture of the electronic circuit 176. In some such embodiments, user interface 180 enables control not only of a specific electrode or of a specific channel, but also of activated subsets of the electrodes.

In some embodiments, user controls and interface 180 includes a pair of anterior intensity buttons 181*a* and 181*b* for respectively increasing and decreasing the intensity of stimulation provided by anterior electrode systems 172, and a pair of posterior intensity buttons 182*a* and 182*b* for respectively increasing and decreasing the intensity of stimulation provided by posterior electrode systems 174. It will be appreciated that user control and interface 180 may include similar intensity buttons for each electrode included in the headset 160.

The user controls and interface 180 may further include a mode changing button 184 for activating and disabling the electronic circuit 176, as well as for changing between modes of operation of headset 160. For example, headset 160 may have multiple preset modes of operation, such as a sleep mode, a maintenance mode, and a treatment mode, and repeated operation of button 184 may switch between these modes, in addition to turning the headset on and off.

A user indication button, for example allowing the user to provide a user indication of pain, discomfort, or reduced paresthesia, may form part of user controls and interface 180 and may be disposed on an exterior surface of anterior member 162.

In some embodiments, the user controls and interface 180 may further include an audio element (not shown), such as a speaker or buzzer, for providing to the user an audible indication of use of the headset 180, such as an indication of activation of the headset, shutting down of the headset, pressing a button on interface 180, changing the stimulation mode, and the like.

As explained hereinabove, the electronic circuit and the user interface are configured to control and/or activate electrodes included in headset 160. In some embodiments, the user interface is configured to control and/or activate at least two, and in some embodiments more than two, pairs of electrodes. As such, in some embodiments, the stimulation circuit and/or the user interface are configured to enable activation of a specific electrode or of a specific pair, or channel, of electrodes, as well as adjustment of the intensity of current supplied by the activated electrodes or of other stimulation parameters of the activated electrodes. In some embodiments, any subset of the electrodes may be activated simultaneously, and in some embodiments specific subsets are predefined, for example during manufacture of the electronic circuit. In some such embodiments, the user interface enables control not only of a specific electrode or of a specific channel, but also of activated subsets of the electrodes.

In some embodiments, electronic circuit 176 includes a transceiver 196, similar to transceiver 116 of FIG. 1A, which transceiver is configured to remotely communicate with a communication device 197 external to headset 160 and similar to external device 150 of FIG. 1A, such as a mobile telephone, a tablet computer, and the like. Communication device 197 may further communicate with a remote storage location, such as a cloud based storage location indicated by reference numeral 198, for storage of data therein or retrieval of data thereof. For example, in some embodiments, data relating to the specific stimulation protocol used for a specific user may be transmitted from transmitter 196 to cloud based storage location 198 for storage therein via communication device 197, and may be retrieved from the cloud based storage location in the future in order to facilitate personalization of the stimulation protocol for the specific user, substantially as described hereinbelow with reference to FIG. 3. As another example, reference data may be transmitted from cloud computing storage location 198 to transceiver 196, for example via communication device 197, in order to facilitate personalization of the stimulation protocol as described herein with reference to FIG. 3.

Figure 2:
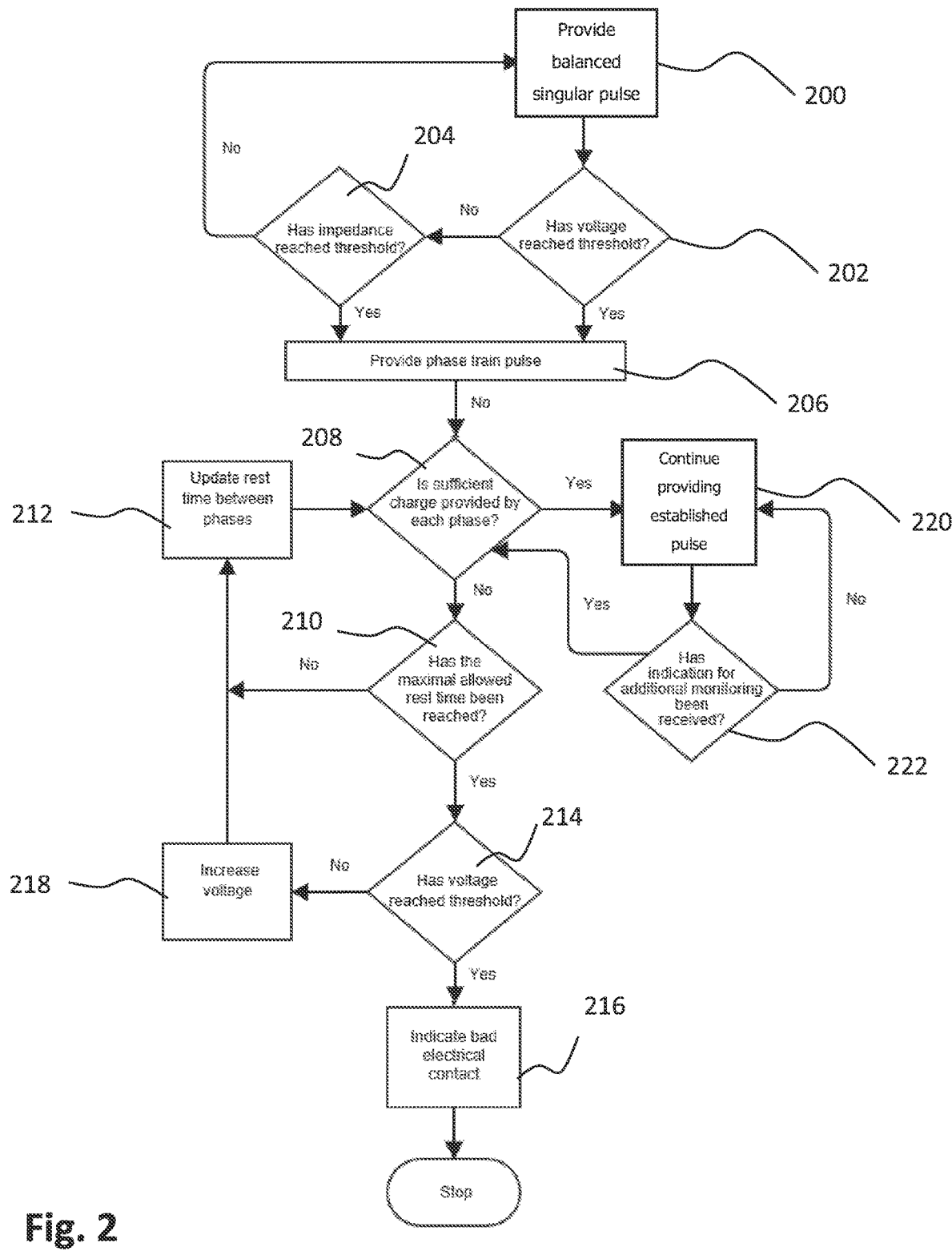
FIG. 2 is a flow chart of an embodiment of a method for neurostimulation of a head region having high impedance according to the teachings herein, using the system of FIG. 1A.

Reference is now made to FIG. 2, which is a flow chart of an embodiment of a method for neurostimulation of a head region having high impedance according to the teachings herein, using the system of FIG. 1A.

Figure 4A:
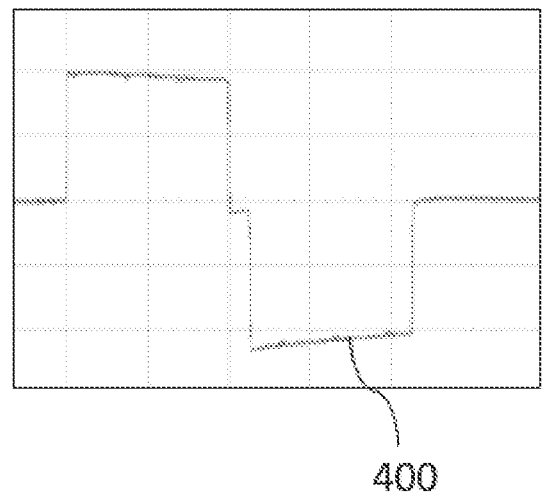

Initially, at step 200, the microcontroller 108 instructs the stimulation circuit 112 to provide, via the stimulation electrodes 102 that engage the user's scalp surface, one or more electrically balanced singular pulses, each having a single positive phase and a single negative phase. An example of such a pulse, provided under standard impedance conditions, is illustrated in FIG. 4A as pulse 400. In some embodiments, the pulse may have an intensity range of 0-60 mA, 0-40 mA, 0-20 m, or 0-15 mA. In some embodiments, the pulse may have a duration of 10-2000 μsec, 100-1600 μsec, 200-1400 μsec, or 300-1000 μsec. In some embodiments, the pulse may have a frequency in the range of 1-20,000 Hz, 1-10,000 Hz, 1-500 Hz, 10-300 Hz, 10-250 Hz, 20-180 Hz, 30-180 Hz or 40-100 Hz.

The microcontroller 108 continuously, periodically or intermittently evaluates whether the voltage required by the electrodes to provide the pulse has reached a predetermined threshold value, or upper voltage threshold, at step 202. The threshold value may be equal to the compliance voltage of the circuit 106, or may be a fraction or percentage thereof. In some embodiments, the threshold value is 60%-70% of the compliance voltage.

In some embodiments, following evaluation of the voltage required by the electrodes to provide the pulse, or concurrently therewith, the microcontroller 108 evaluates whether the impedance in the system has reached a predetermined impedance threshold value, at step 204. This would be suitable when predetermined impedance is reached even if voltage threshold is not reached, for example if the pulse is provided at a relatively low current. In some embodiments, the impedance threshold may be greater than 8KΩ, greater than 10KΩ or greater than 12KΩ.

If the voltage has not reached the voltage threshold, and the impedance has not reached the impedance threshold, the microcontroller 108 instructs the stimulation circuit 112 to continue providing, via the stimulation electrodes 102, a balanced singular pulses at step 200.

Figure 4B:
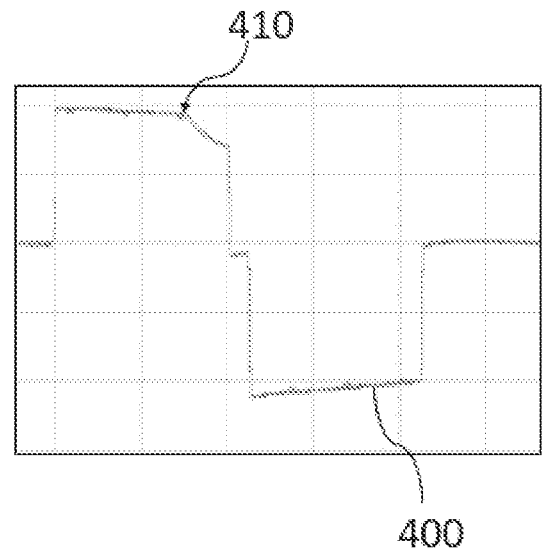
Figure 4C:
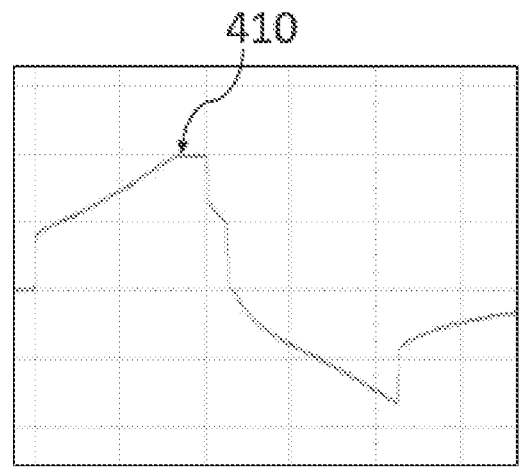

It will be appreciated that when the voltage in the system is insufficient for providing the pulse, or if the impedance in the system is too high, then according to Ohm's law the current provided by the electrodes will be insufficient to allow for the full charge to be provided to the tissue. FIG. 4B illustrates an example of the current provided by singular pulse 400 under high impedance conditions, and as can be seen, the positive phase of the pulse is cut beginning at a time point indicated by reference numeral 410, such that the pulse does not provide the charge intended to be provided. FIG. 4C illustrates the voltage on the electrodes 102 under high impedance conditions, and as seen the voltage required by the electrodes rises until an upper voltage threshold is reached. In the illustrated embodiment, the upper voltage threshold is the compliance voltage of the system. Comparison of FIGS. 4B and 4C demonstrates that the time point 410, where the pulse becomes cut (FIG. 4B), corresponds to the time at which the compliance voltage was reached (FIG. 4C).

Figure 5A:
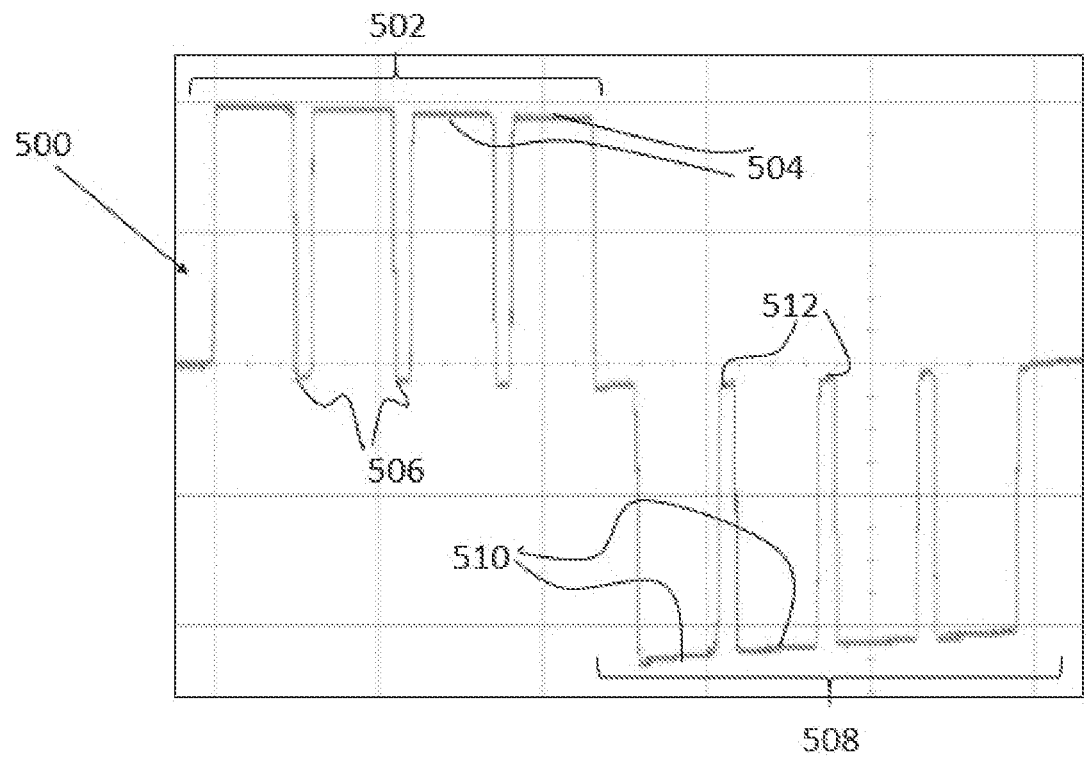

As such, if the evaluation at step 202 determines that the voltage has reached the voltage threshold, and/or if the evaluation at step 204 determines that the impedance has reached the impedance threshold, the pulse provided by the electrodes 102 will be cut. Consequently, at step 206 the microcontroller 108 instructs the stimulation circuit 112 to change the pulse provided via electrodes 102 to be a phase train pulse, similar to the pulse shown in FIG. 5A. Referring also to FIG. 5A, it is seen that the pulse now provided by the electrodes 102 is a balanced pulse 500 including a positive phase train 502 immediately followed by a negative phase train 508. The positive phase train 502 includes a streak of constant current positive phases 504 separated by rest times 506, and the negative phase train 508 includes a streak of constant current negative phases 510 separated by rest times 512. Each of the positive phases 504 and the negative phases 510 is intended to provide a predetermined amount of charge. It will be appreciated that the term "predetermined amount of charge" relates to an amount of charge equal to the intended amount of charge, as well as to an amount of charge differing from the intended amount of charge by at most 15%, at most 10%, at most 5%, at most 3%, or at most 1%.

The inventors have found that the transition from the singular pulse of FIG. 4A to the phase-train pulse of FIG. 5A results in the reduction of the impedance of the layers underlying the electrodes, such as the hair and tissue layers, and consequently in reduction of the voltage required to provide the required charge. As such, as seen in FIG. 5A, in each of the phases 504 and 510 the pulse is complete, and the intended amount of charge, or an amount of charge deviating from the intended amount of charge by at most 15%, at most 10%, at most 5%, at most 3%, or at most 1% is provided to the scalp of the user.

It is a particular feature of the teachings herein that a time ratio $tr^p$ between a cumulative duration $d_{rt}^p$ of the rest times 506 between the positive phases 504 and a cumulative duration $d_s^p$ of the positive phases 504 is smaller than a predetermined ratio. Similarly, a time ratio $tr^n$ between a cumulative duration $d_{rt}^n$ of the rest times 512 between the negative phases 510 and a cumulative duration $d_s^n$ of the negative phases 510 is smaller than a predetermined threshold ratio. In some embodiments, the predetermined threshold ratio is in the range of 0.4-1.2, 0.5-1 or 0.55-0.75. In some embodiments, the predetermined threshold ratio is 0.6, as explained hereinbelow in Example 1.

In some embodiments, such as the embodiment of FIG. 5A, the positive phases 504 and the negative phases 510 have a common phase width $w_l$. However, in other embodiments, the positive phases 504 may have a common phase width $w_p$, which may be different from a common phase width $w_n$ of the negative phases 510. In yet further embodiments, the positive phases need not have a common phase width, and the negative phases need not have a common phase width. It will be appreciated that for the purposes of this specification and the claims that follow the term "common phase width" relates to an equal phase width, but also includes phase widths with at most 20%, at most 15%, at most 10%, at most 5%, or at most 1% deviation from one another.

In some embodiments, the rest times 506 between immediate successor positive phases 504 and the rest times 512 between immediate successor negative phases 510 have a common rest-time value $rt^l$. In other embodiments, the rest times 506 between immediate successor positive phases 504 have a common rest time value $rt^p$, which may be different from a common rest time value $rt^n$ of the rest times 512 between immediate successor negative phases 510. In yet further embodiments, the rest times 506 need not have a common rest time value, and the rest times 512 need not have a common rest time value. It will be appreciated that for the purposes of this specification and the claims that follow the term "common rest time value" relates to an equal rest time values, but also includes rest time values with at most 20%, at most 15%, at most 10%, at most 5%, or at most 1% deviation from one another.

In some embodiments, a duration of the positive phase train 502 is equal to a duration of the negative phase train 508, though it need not necessarily be equal. In some embodiments, the cumulative duration $d_s^p$ of the positive phases 504 is equal to the cumulative duration $d_s^n$ of the negative phases 510, though it need not necessarily be equal. In some embodiments, the cumulative duration $d_{rt}^p$ of the rest times 506 between the positive phases 504 is equal to the cumulative duration $d_{rt}^n$ of the rest times 512 between negative phases 510, though it need not necessarily be equal.

The number of positive phases 504 in positive phase train 502, and the number of negative phases 510 in negative phase train 508, is in the range of 2-30. In some embodiments, the number of positive phases 504 in positive phase train 502 is equal to the number of negative phases 510 in negative phase train 508, though it need not necessarily be equal.

In some embodiments, the duration of each rest time 506 or 512 is at least 5 μsec. In some embodiments, the phase width of each positive phase 504 and of each negative phase 510 is at most 600 μsec, at most 400 μsec, at most 300 μsec, at most 200 μsec, at most 100 μsec, or at most 50 μsec.

Returning to FIG. 2, following transition to a phase-train pulse at step 206, the results of the transition are evaluated in an attempt to reach a pulse which requires the lowest voltage, while providing sufficient charge to the user's scalp. As such, at step 208 the microcontroller 108 evaluates, or monitors, whether sufficient charge is being provided by each of the positive phases 504 and the negative phases 510. It will be appreciated that the charge is considered sufficient if it is equal to the intended charge, or if it deviates from the intended charge by at most 15%, at most 10%, at most 5%, at most 3%, or at most 1%.

In some embodiments, the charge provided by the phases is monitored by sensing electrodes 104, which, in some embodiments, may be the same electrodes as stimulating electrodes 102. In some embodiments, the charge is monitored by an additional sensor, external to the stimulating electrodes 102 and sensing electrodes 104, which is functionally associated with circuit 106, such as for example a sensor in sensor array 124.

Figure 5B:
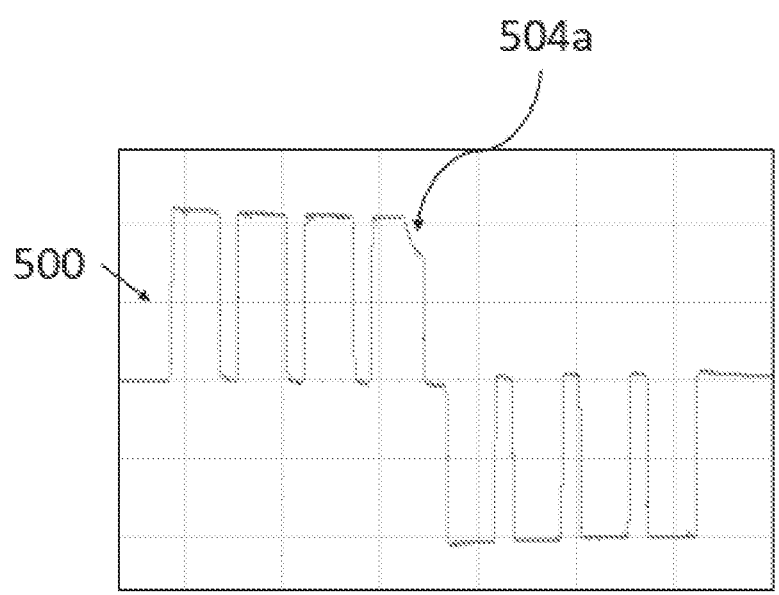

In some embodiments, the charge is monitored by monitoring a waveform of each provided phase, to identify whether the provided waveform for the phase is identical to an intended waveform, or deviates from the intended waveform by at most 15%, at most 10%, at most 5%, at most 3%, or at most 1%. In some embodiments, a reduction in the charge provided to the scalp, or insufficient charge, is indicated by the provided waveform differing from the intended waveform more than the permissible deviation, and specifically by the provided waveform dropping, or being "cut", toward the end of a phase. Referring additionally to FIG. 5B, which shows the phase train pulse 500 of FIG. 5A in a situation where insufficient charge is provided, it is seen that the waveform of positive phase 504a does not form a right angle at the end, or is incomplete, which is indicative of the charge being provided by the phase 504a to the scalp being less than the intended charge.

If at step 208 it is determined that insufficient charge is being provided, for example by determining that the waveform of the pulse is similar to that shown in FIG. 5B, at step 210 the microcontroller 108 evaluates whether the time ratio $tr^p$, between the cumulative duration $d_{rt}^p$ of the rest times between the positive phases and the cumulative duration $d_s^p$ of the positive phases, and the time ratio $tr^n$, between the cumulative duration $d_{rt}^n$ of the rest times between the negative phases and the cumulative duration $d_s^n$ of the negative phases, are smaller than a predetermined threshold ratio. Stated differently, at step 210 the microcontroller 108 evaluates whether the cumulative rest time in the pulse is less than the maximal allowed rest time, or is equal to the maximal allowed rest time.

If at step 210 the microcontroller 108 determines that the maximal allowed rest time has not been reached, at step 212 the microcontroller 108 instructs the stimulation circuit 112 to update at least one rest time in the provided pulse. Due to the fact that the maximal allowed rest time has not been reached, the microcontroller updates the pulse by increasing at least one rest time in the positive phase train and/or in the negative phase train.

In some embodiments, the microcontroller 108 instructs the stimulation circuit 112 to update the pulse by increasing all the rest times in the positive phase train, and/or all the rest times in the negative phase train. In some embodiments, the microcontroller 108 instructs the stimulation circuit 112 to increase the common rest time value $rt^p$ in the positive phase train, the common rest time value $rt^n$ in the negative phase train, or the common rest time value $rt^t$ in the pulse.

Figure 5C:
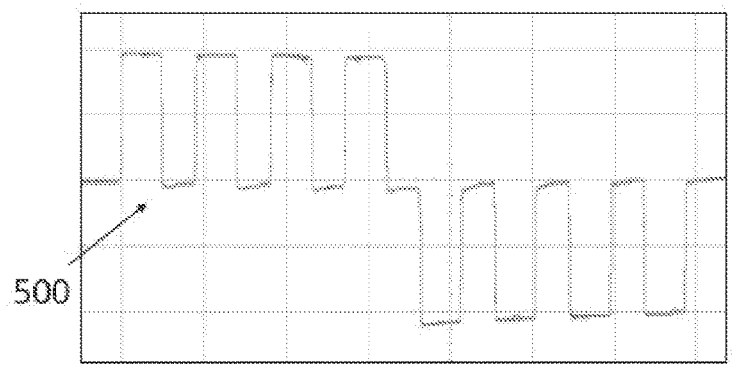

FIG. 5C illustrates the phase train pulse 500 of FIGS. 5A and 5B, following an increase in the common rest time between the phases. As seen in FIG. 5C, in some cases, following the increase in the rest times, the pulse waveform is once again "complete" and the expected amount of charge is being provided by the pulse to the scalp of the user.

If the maximal allowed rest time has been reached at step 210, at step 214 the microcontroller 108 evaluates whether the voltage provided by the electrodes has reached a predetermined voltage threshold, such as the compliance voltage of the system or a predetermined fraction or percentage thereof.

If at step 214 the microcontroller 108 determines that the voltage threshold has been reached, that means that the rest times cannot be increased (due to the determination at step 210), and the voltage cannot be increased (due to the determination at step 214). As such, it is likely that there is a bad electrical contact between the electrodes 102 and the user's scalp, or another malfunction in the system, and at step 216 the microcontroller 108 may provide to the user an indication of such a malfunction or bad electrical contact, for example via user interface 134. Subsequently, treatment is aborted.

Alternately, if at step 214 the microcontroller 108 determines that the voltage threshold has not been reached, at step 218 the microcontroller 108 instructs the stimulation circuit 112 to increase the voltage to be applied by electrodes 102, and subsequently updates at least one rest time in the provided pulse at step 212. In some embodiments, due to the fact that the maximal allowed rest time has been reached, the microcontroller 108 instructs the stimulation circuit 112 to update the pulse by reducing at least one of the rest times in the positive phase train and/or in the negative phase train.

In some embodiments, the microcontroller 108 instructs the stimulation circuit 112 to update the pulse by reducing all the rest times in the positive phase train, and/or all the rest times in the negative phase train. In some embodiments, the microcontroller 108 instructs the stimulation circuit 112 to reduce the common rest time value $rt^p$ in the positive phase train, the common rest time value $rt^n$ in the negative phase train, or the common rest time value $rt^t$ in the pulse.

In some embodiments, following the increase in voltage at step 218, and the reduction in the rest time at step 212, the phase train pulse has the waveform shown in FIG. 5A.

In some embodiments, any rest time reduced by the microcontroller 108 or by stimulation circuit 112 is reduced to a minimal rest time, which, in some embodiments, is not less than 5 μsec.

It will be appreciated that in some embodiments, the change to the rest times is carried out by microcontroller 108 instructing the stimulation circuit 112 to change one or both of the time ratio $tr^p$, between a cumulative duration $d_{rt}^p$ of the rest times 506 between the positive phases 504 and a cumulative duration $d_s^p$ of the positive phases 504, and the time ratio $tr^n$, between a cumulative duration $d_{rt}^n$ of the rest times 512 between the negative phases 510 and a cumulative duration $d_s''$ of the negative phases 510.

In some embodiments, at step 212 the microcontroller 108 may instruct the stimulation circuit 112 to adapt additional characteristics of the pulse. In some embodiments, at step 212 the microcontroller 108 may also instruct the stimulation circuit 112 to adapt the number of positive phases in the positive phase train and/or the number of negative phases in the negative phase train. In some embodiments, at step 212 the microcontroller 108 may also instruct the stimulation circuit 112 to adapt the phase width of one or more of the positive phases, or a common phase width $w_P$ of the positive phases. In some embodiments, at step 212 the microcontroller 108 may also instruct the stimulation circuit 112 to adapt the phase width of one or more of the negative phases, or a common phase width $w_n$ of the negative phases. In some embodiments, the microcontroller 108 may also instruct the stimulation circuit 112 to adapt the amplitude of one or more of the positive phases and/or of one or more of the negative phases.

Following the change to the rest times applied by the microcontroller 108 at step 212, the microcontroller 108 continues to evaluate whether or not sufficient charge is provided by each phase of the pulse at step 208, and additional updates to the rest-time and/or voltage may be applied.

At any occurrence of step 208, if the microcontroller 108 determines that sufficient charge is being provided by each phase of the pulse to the scalp of the user, at step 220 the microcontroller 108 instructs the stimulation circuit 112 to continue to provide the pulse as established.

The microcontroller 108 then waits for an indication that additional monitoring is required, at step 222. When such an indication is provided, the microcontroller returns to step 208 and assesses whether the pulse is providing sufficient charge, and flow continues from there as described hereinabove. Otherwise, the microcontroller continues to provide the established pulse.

In some embodiments, the indication is a microcontroller-internal indication, for example a time indication for periodic monitoring, for example provided every 10 minutes, every 5 minutes, or every 3 minutes. In some such embodiments, additional monitoring may be carried out more frequently at the initial part of the treatment, and then carried out less frequently at later stages of the treatment once the system has reached an equilibrium.

In other embodiments, the indication may be received from a component external to the microcontroller. For example, the indication may be an indication of discomfort, pain, or reduced paresthesia, provided by the user, via user interface 134.

In some embodiments, the indication may be provided by a sensor sensing a change in the system. For example, microcontroller 108 may receive from a humidity sensor forming part of sensor array 124 a signal indicating a change in the humidity in the vicinity of electrodes 102, which requires additional monitoring. As another example, microcontroller 108 may receive from a temperature sensor forming part of sensor array 124 a signal indicating a change in the temperature in the vicinity of electrodes 102, which requires additional monitoring. As a further example, microcontroller 108 may receive from a pressure sensor forming part of sensor array 124 a signal indicating a change in the pressure applied to electrodes 102, which requires additional monitoring. As yet another example, the microcontroller 108 may receive from an accelerometer forming part of sensor array 124 a signal indicating a change in the position of the user or in the position of the electrodes, which may indicate that additional monitoring is required (for example, if the user was supine and is now standing, less pressure is applied to the electrodes, which may increase the impedance).

It will be appreciated that in order to evaluate the quality of signal transduction in the system (at step 208), one may replace the evaluation of the charge provided by the phases of the pulse with an evaluation of the impedance in the system, which, due to Ohm's law, is equivalent to the evaluation of the charge. In such embodiments, the rest times in the provided pulse and/or voltage of the provided pulse would be updated if the impedance measured between the electrodes 102 is above a predetermined impedance threshold. In some embodiments, the impedance threshold may be greater than 8KΩ, greater than 10KΩ or greater than 12KΩ.

Figure 3:
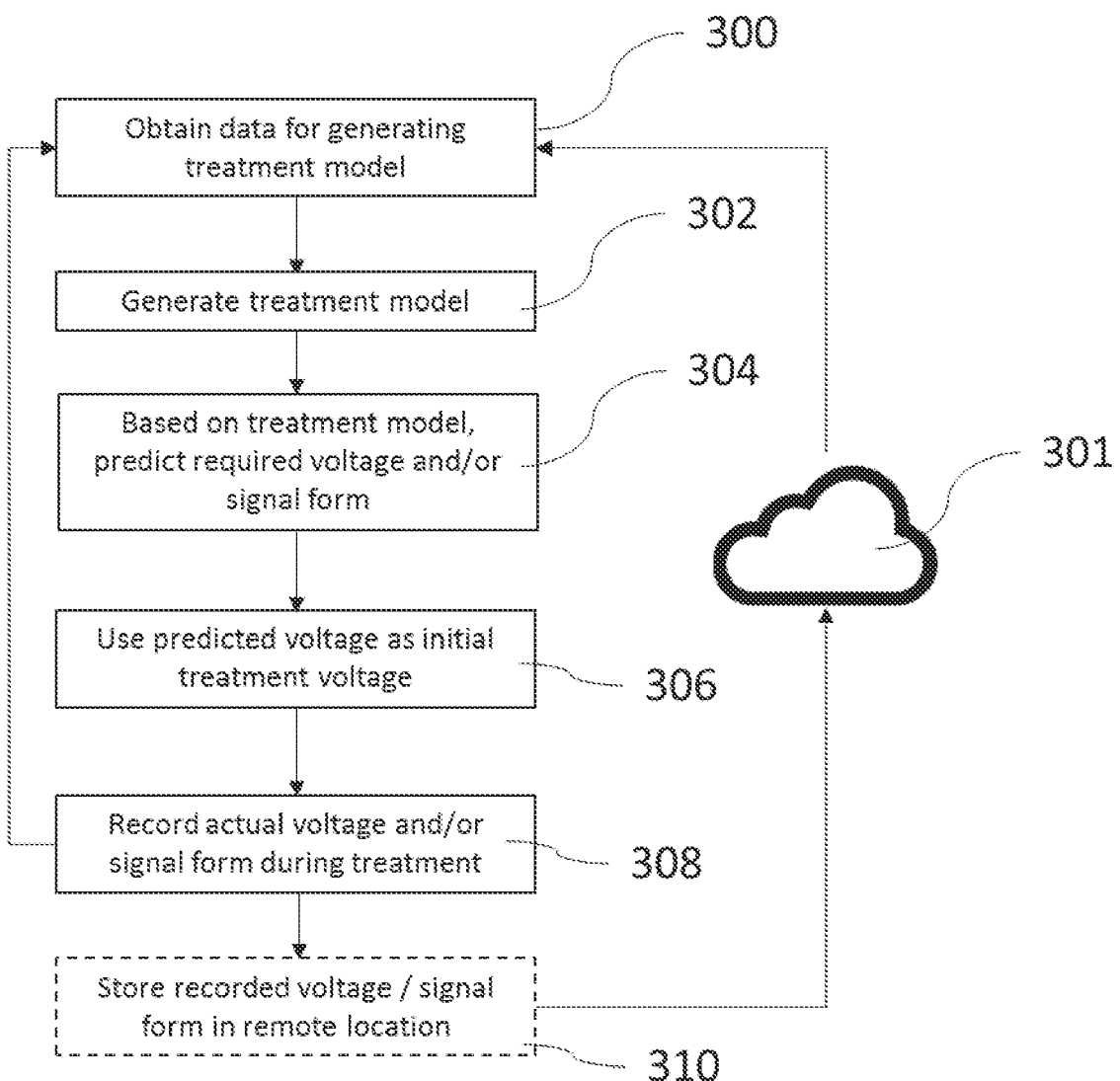
FIG. 3 is a flow chart of an embodiment of a method for personalization of the method of FIG. 2 according to the teachings herein.

Reference is now made to FIG. 3, which a flow chart of an embodiment of a method for personalization of the method of FIG. 2 according to the teachings herein.

As seen at step 300, initially, data for generating a treatment model for a specific user is obtained. In some embodiments, the data may be obtained from a remote database, either based in a server or Cloud based. In some embodiments, the data may be based on specific information relating to the user, such as characteristics of the patient such as age, weight, and hair type, and values collected during previous treatments such as stimulation intensity, impedance levels reached, voltage levels reached, changes in voltage/impedance during treatment, and/or treatment duration.

Subsequently, at step 302, a treatment model is generated based on default values modified in accordance with the obtained data. In some embodiments, the treatment model takes into consideration currently collected treatment data, such as information relating to the current state of the system as identified by sensors in the system (e.g. sensors in sensor array 124), which information may include humidity information as identified by a humidity sensor, temperature information as identified by a temperature sensor, position information as identified by an accelerometer, and the like. Additionally, the system may allow the user to provide input, for example via user interface 134, relating to the current state of the system, and to use the input to generate the treatment model. For example, the user may indicate that skin irritation or excess skin erythema occurred, which can be used to update the treatment model for this specific user.

At step 304, the microcontroller of the system generates a prediction of the voltage and/or pulse form that will be required in order to provide sufficient charge to the specific user's scalp, while using a reasonable voltage and short rest times between phases. At step 306, the prediction is used to initiate treatment in accordance with the method of FIG. 2, where the predicted voltage is used as the initial voltage in the treatment.

At step 308, during and/or after treatment, the actual voltage required in order to provide sufficient charge to the user's scalp and/or parameters of the actual waveform used to provide such charge (for example the number of positive and negative phases, the length of each positive and negative phase, the lengths of the rest times between phases, and the like) are recorded by the microcontroller, and stored in a memory associated therewith.

In some embodiments, the recorded data may be transmitted to a remote database, either located at a remote server or Cloud based, as seen at step 310. The data may be stored in the remote database, in some embodiments associated with at least one identifier of the specific user, such as an identification number or name of the user, or with at least one identifier of the device used by the user, so that it may be readily used in the next treatment session, for example as the data obtained at step 300.

Reference is now made to the following example, which together with the above description, illustrates the invention in a non-limiting fashion.

Example

Ten users were treated using the system of FIG. 1B and the method of FIG. 2.

The treatment included stimulation of the greater occipital nerve. A headset, similar to that shown in FIG. 1B, was placed on each user's head so that the posterior electrodes were placed under the hair over the left and right greater occipital nerve branches at the level of the external occipital protuberance.

Stimulation in the form of electrically balanced pulses was applied at a constant current of 5 mA and at a frequency of 80 Hz.

In a baseline round, the provided positive and negative phases were singular phases each having a phase duration of 400 μsec, as described hereinabove with reference to FIG. 4A. The voltage level was recorded. The users were asked to note the intensity of paresthesia felt at the nerve distribution region, and this intensity was considered baseline intensity and assigned a score of 10.

In each subsequent round of treatment, the pulse included a positive phase train and a negative phase train as described hereinabove with reference to FIG. 5A. The cumulative duration of the stimulation phases, or the "on-time" in each of the positive and negative phase trains, remained 400 μsec. In each round, the cumulative rest time in each phase train was increased, and the resulting change in voltage required to provide the pulse was recorded. Additionally, the users were asked to assign a score of 1-10 to the paresthesia felt in the nerve distribution region, where 10 is the baseline paresthesia and 1 is negligible paresthesia.

Figure 6A:
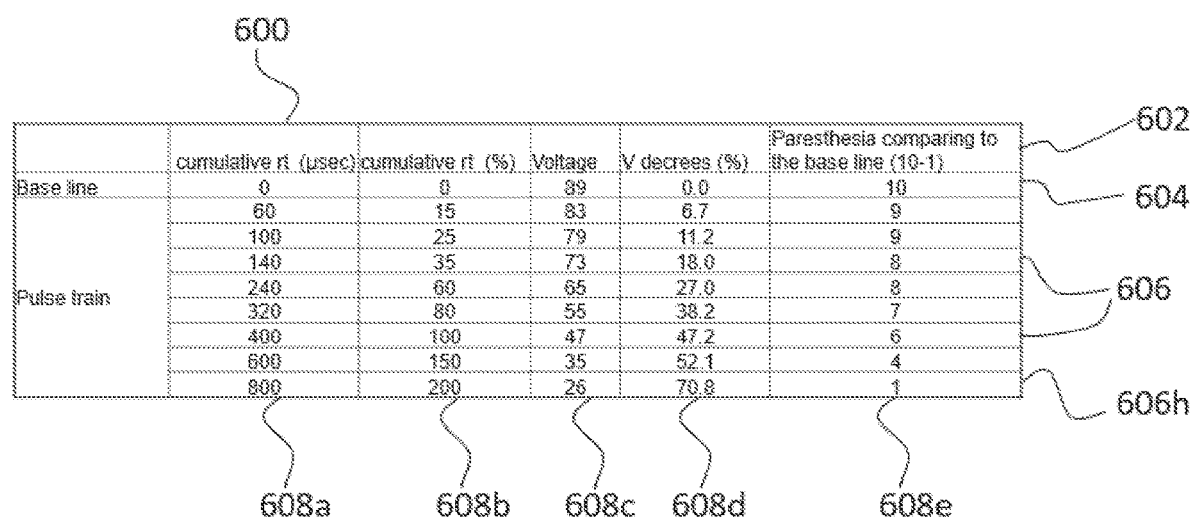
FIG. 6A illustrates a table including experimental results showing the change in voltage and in paresthesia following changes to the provided pulse, the experimental results obtained using the system of FIG. 1A and the method of FIG. 2.

The results are summarized in FIG. 6A, which illustrates a table including the change in voltage and in paresthesia following the change to the cumulative rest time of the provided pulse.

The table 600 includes a title row 602, a first baseline row 604, and a plurality of treatment rows 606, each relating to a single round of treatment. Each of the rows is divided into a plurality of columns 608, including:

column 608a showing the cumulative rest time, in μsec, in each of the positive and negative phase trains in that round of treatment;

column 608b showing the percentage of the cumulative length of the rest time from the cumulative phase durations, or, stated differently, the percentage of the "off time" from the "on time" for each of the positive and negative phase trains—for example, if the cumulative rest time is 100 μsec, and as mentioned above the cumulative phase duration in each phase train in all the rounds is 400 μsec, then the percentage shown in column 608b would be 25%;

column 608c showing the average voltage required in order to provide sufficient charge, given the rest time specified in column 608a;

column 608d showing the percent of decrease in average voltage, relative to the baseline voltage; and column 608e showing the average paresthesia score provided by users for the treatment round.

Figure 6B:
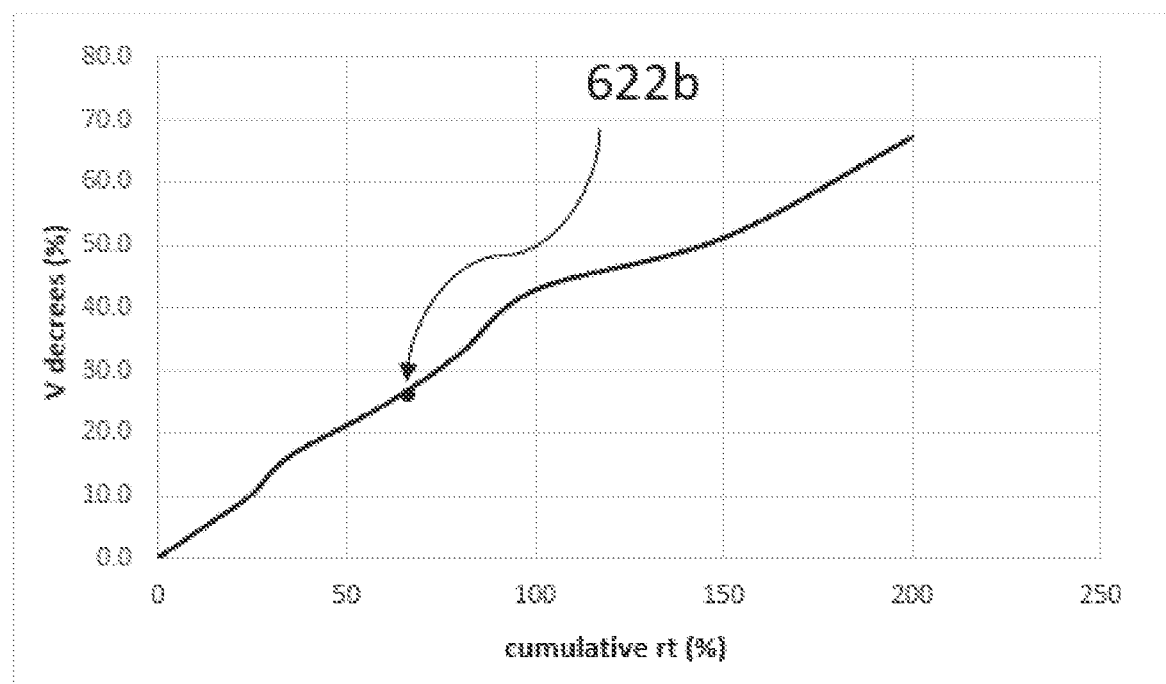
FIGS. 6B and 6C provide schematic graphic representations of the change in voltage as a result of the change in the pulse and of a change in paresthesia as a result of a change in the pulse, the data for FIGS. 6B and 6C derived from the table of FIG. 6A.
Figure 6C:
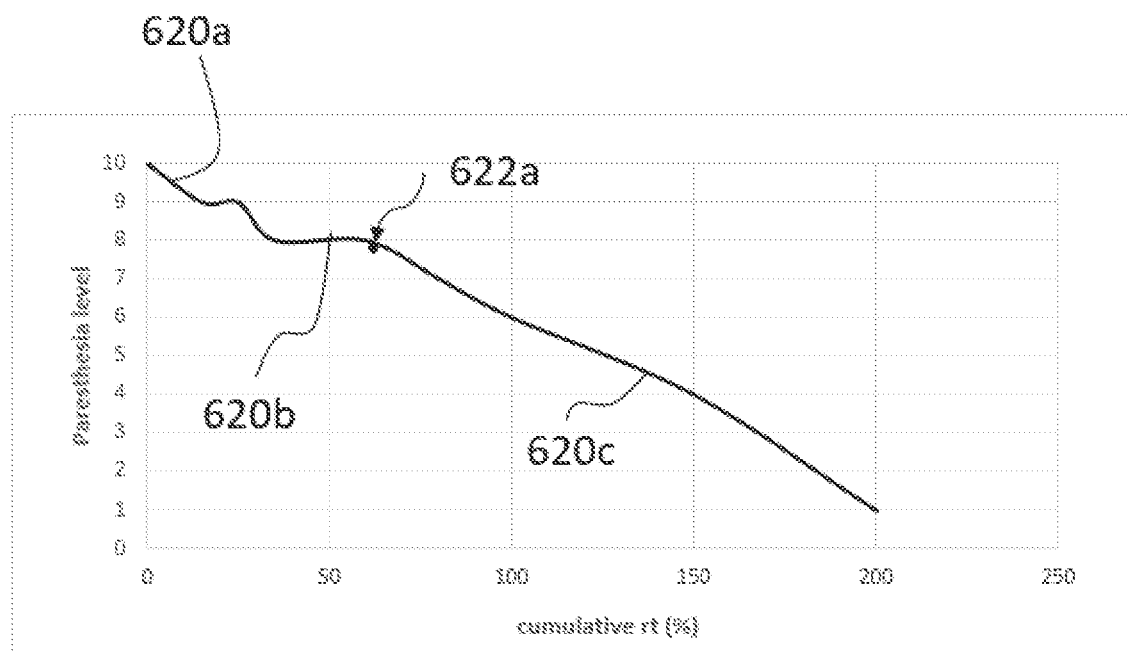

FIGS. 6B and 6C provide schematic graphic representations of the results shown in FIG. 6A. Specifically, FIG. 6B illustrates the change in voltage as a result of the change in the pulse waveform in the different treatment rounds, and FIG. 6C illustrates the change in experienced paresthesia as a result of a change in the pulse waveform in each pulse round.

A closer look at table 600 shows that as the cumulative rest time increases, the voltage required in order to provide sufficient charge to the scalp of the user decreases, as well as the paresthesia experienced by the user. Looking specifically at the lowest row 606h of the table 600, it is seen that the voltage required to provide the pulse, when the cumulative rest time is double the length of the cumulative phase duration, has decreased by as much as 67%, and the paresthesia experienced by the user has decreased entirely, to the point that the users only felt negligible paresthesia, if any.

As seen in FIG. 6C, the paresthesia experienced by the users (y-axis) is plotted against the percentage of the total rest time from the total phase duration, or stated differently, the percentage of the total "off time" from the total "on time" (x-axis). As seen, the graph initially decreases at section 620a, then plateaus at section 620b, and subsequently decreases at section 620c, substantially linearly, until reaching the score of 1.

As seen, at the point of the plateau having the greatest rest time percentage, indicated in FIG. 6C by reference numeral 622a, the user still experiences significant paresthesia (with an average score of 8). In the present example, this point is at a rest time percentage of 60%, or a ratio of 0.6 between the cumulative rest time and the cumulative phase duration.

Turning to FIG. 6B, it is seen that the percentage of decrease of the voltage required to provide sufficient charge from voltage baseline (y-axis) is plotted against the percentage of the total rest time from the total phase duration, or stated differently, the percentage of the total "off time" from the total "on time" (x-axis). At point 622b, which corresponds in the rest time percentage to point 622a of FIG. 6C, the voltage required to provide sufficient charge to the user's scalp is approximately 25% lower than the baseline voltage.

It will be appreciated that in accordance with the illustrated results, the identified rest time percentage of 60% is particularly suitable as the rest time threshold as it significantly reduces the voltage required in order to provide sufficient charge to the user's scalp, while the user continues to feel significant levels of paresthesia in the nerve distribution region, which is desirable.

As used herein in the specification and in the claims section that follows, the term "or" is considered as inclusive, and therefore the phrase "A or B" means any of the groups "A", "B", and "A and B".

As used herein in the specification and in the claims section that follows, the term "pulse" relates to an electrical signal, for example applied via an electrode or sensed by an electrode.

As used herein in the specification and in the claims section that follows, the term "phase" relates to a pulse or a portion thereof, having current starting from a zero amplitude, changing to a higher amplitude, and returning to zero amplitude.

As used herein in the specification and in the claims section that follows, the term "positive phase" relates to a phase providing current which flows in the positive direction.

As used herein in the specification and in the claims section that follows, the term "negative phase" relates to a phase providing current which flows in the negative direction.

As used herein in the specification and in the claims section that follows, the term "balanced pulse" relates to a pulse including a positive portion including at least one positive phase and a negative portion including at least one negative phase, such that the magnitude, or charge, of the positive and negative portions is equal, or is within 15%, within 10%, within 5%, within 3%, or within 1% of one another.

As used herein, in the specification and in the claims section that follows, the term "phase train" relates to a pulse including two or more consecutive phases of the same type or magnitude, or in the same direction. For example, a positive phase train includes two or more consecutive positive phases and a negative phase train includes two or more consecutive negative phases. Any phases in the opposite direction, having a charge of up to 30% of the charge of the lowest-charge phase in the phase train, are considered as noise and are disregarded when defining a phase train and identifying consecutive phases. For example, a pulse including two positive phases, then a very small short negative phase, and then additional phases, would be considered a positive phase train, because the small short negative phase is disregarded.

As used herein, in the specification and in the claims section that follows, the term "phase train pulse" relates to a pulse including at least one positive phase train and at least one negative phase train.

As used herein, in the specification and in the claims section that follows, the term "balanced phase train pulse" relates to a balanced pulse including at least one positive phase train and at least one negative phase train.

As used herein, in the specification and in the claims section that follows, the term "singular pulse" relates to a pulse including a single positive phase and/or a single negative phase, and not including a phase train.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Similarly, the content of a claim depending from one or more particular claims may generally depend from the other, unspecified claims, or be combined with the content thereof, absent any specific, manifest incompatibility therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A head mounted device for transdermally applying electrical stimulation to a region of a head of a user, the head of the user including a scalp, the head mounted device comprising:
    at least a pair of electrodes, configured, when the head mounted device is donned, to engage the scalp of the user and to deliver, via the scalp of the user, a balanced pulse comprising a positive phase train including a streak of constant current positive phases separated by rest times, said positive phase train immediately followed by a negative phase train including a streak of constant current negative phases separated by rest times, each of said positive phases and said negative phases being for providing a predetermined amount of charge to the head of the user;
    at least one sensor adapted, when said head mounted device is donned by said user and during transmission of said pulse, to engage the skin of the scalp and to monitor an amount of charge delivered by said positive phases and said negative phases;
    an electronic circuit, functionally associated with said at least two electrodes and having a compliance voltage; and
    a processing unit, functionally associated with said electrodes to provide instructions thereto and with said at least one sensor to receive input therefrom, said processing unit programmed to:
        (a) provide an input causing said electrodes to deliver said balanced pulse via the scalp of the user;
        (b) calculate a first time ratio ($tr^p$) between a cumulative duration ($d_{rt}^p$) of said rest times between said positive phases in said positive phase train and a cumulative duration ($d_s^p$) of said positive phases ($tr^p = d_{rt}^p : d_{rt}^p$), and a second time ratio ($tr^n$) between a cumulative duration ($d_{rt}^n$) of said rest times between said negative phases in said negative phase train and a cumulative duration ($d_s^n$) of said negative phases ($tr^n = d_{rt}^n : d_s^n$), wherein, at least initially, each of said first and second time ratios is smaller than a predetermined threshold ratio;
        (c) receive input from said at least one sensor, the input indicative of an amount of charge delivered by said positive phases and said negative phases;
        (d) identify said received input which is indicative of a reduction of charge delivered by one or more of said positive and said negative phases;
        (e) upon identification of said reduction, provide input to said electrodes causing said electrodes to adapt at least one said rest time in at least one of said positive phase train and said negative phase train;
        (f) calculate a first updated value for said first time ratio and a second updated value for said second time ratio, following adaptation of at least one said rest time; and
        (g) repeat steps (a)-(f) using said at least one of said rest time following said adaptation, until:
            said processor identifies that said predetermined amount of charge has been provided by each of said positive and said negative phases; or
            at least one of said first updated value of said first time ratio and said second updated value of said second time ratio reaches said predetermined threshold ratio and a voltage of said balanced pulse reaches a predetermined voltage threshold.

2. The device of claim 1, said electrodes configured to deliver said balanced pulse wherein said positive phases in said positive phase train and said negative phases in said negative phase train have a common phase width $w_l$.

3. The device of claim 1, said electrodes configured to deliver said balanced pulse wherein said rest times between immediate successor phases in said positive phase train and in said negative phase train have a common rest-time value $rt^l$.

4. The device of claim 1, wherein:
    when each of said first and second time ratio are less than said predetermined threshold ratio, said processing unit is configured to provide said input to said electrodes causing said electrodes to increase a duration of said at least one said rest-time; and when each of said first and said second time ratio are equal to or greater than said predetermined threshold ratio, said processing unit is configured to provide said input to said electrodes causing said electrodes to increase a voltage provided by said electrodes and to decrease a duration of said at least one said rest time to a predetermined minimum rest-time value.

5. The device of claim 1, wherein said processing unit is further programmed to provide input to said electrodes causing said electrodes to adapt to a phase width of at least one said positive phase or at least one said negative phase.

6. The device of claim 1, wherein the region of the head is a hair covered region of the head.

7. The device of claim 6, wherein said electrodes are configured, when the head mounted device is donned, to engage said hair covered region of the head.

8. The device of claim 1, wherein said region of the head comprises a cephalic nerve, such that said electrodes are configured to deliver said electrical stimulation to said cephalic nerve in said region of the head.

9. The device of claim 1, said electrodes configured to deliver said balanced pulse having at least one of the following characteristics:
   a duration of each said rest time in said positive phase train and in said negative phase train is at least equal to a minimum rest time duration; and
   a phase width of each of said positive phases and of each of said negative phases is not greater than a maximal phase width.

10. The device of claim 1, wherein said at least one sensor is at least one of said electrodes.

11. The device of claim 1, wherein said at least one sensor is external to said electrodes and is functionally associated with said electronic circuit.

12. The device of claim 1, wherein said at least one sensor is configured to monitor a provided waveform of each of said positive and said negative phases, and wherein said processing unit is configured to identify, for each said positive and said negative phase, whether the provided waveform is identical to an intended waveform, and to identify said reduction of charge if said provided waveform is not identical to said intended waveform.

13. The device of claim 1, wherein said processing unit is configured to provide to said electrodes instruction for adapting at least one of said first time ratio and said second time ratio.

14. The device of claim 1, wherein said processing unit is configured to provide to said electrodes instructions for changing at least one of:
   a number of said positive phases in said positive phase train; and
   a number of said negative phases in said negative phase train.

15. The device of claim 1, wherein said processing unit is configured to provide to said electrodes instructions for changing an amplitude of at least one of said positive phases and said negative phases.

16. The device of claim 1, wherein said device has at least one of the following characteristics:
   said at least one sensor is configured to monitor impedance in said electronic circuit, and said processing unit is configured to identify said impedance exceeding an impedance threshold; and
   said at least one sensor is configured to monitor a voltage delivered by said electrodes, and said processing unit is configured to identify said voltage reaching an upper voltage threshold.

17. The device of claim 1, wherein:
   following said processing unit identifying that said predetermined amount of charge has been provided by each of said positive and said negative phases and completion of said step (g), said processing unit is configured to receive additional input at least from said at least one sensor and to identify at least one of a change in the charge delivered by said positive and said negative phases and a change in conditions in which said positive and said negative phases are provided; and
   following said processing unit identifying said change in conditions, said processing unit is further configured to repeat said steps (e) to (g).

18. The device of claim 1, further comprising at least one of:
   a user interface functionally associated with said processing unit, wherein said additional input comprises input provided by the user via said user interface; and
   a sensor functionally associated with said processing unit and configured to sense conditions in an area adjacent to said electrodes, and wherein said additional input comprises a signal provided from said sensor to said processing unit, the signal indicating a change in sensed conditions in an area adjacent said electrodes.

19. The device of claim 1, further comprising a user interface functionally associated with said processing unit and wherein, following at least one of said first time ratio and said second time ratio reaching said predetermined threshold ratio and said voltage reaching said predetermined voltage threshold, said processing unit provides to the use ran indication of malfunction and terminates application of said electrical stimulation.

20. The device of claim 1, wherein:
   said electrodes are configured to deliver, prior to delivery of said positive phase train and said negative phase train, a balanced singular constant-current pulse comprising a positive phase immediately followed by a negative phase, each of said positive and negative phases being for providing a predetermined amount of charge to the head of the user, and
   said processing unit is configured to identify, prior to delivery of said positive phase train and said negative phase train, at least one of:
   that impedance in said electronic circuit during delivery of said singular pulse has reached a predetermined impedance threshold; and
   that a voltage required to deliver said singular constant current pulse has reached an upper voltage threshold.

* * * * *